(12) United States Patent
Martin et al.

(10) Patent No.: US 8,510,126 B2
(45) Date of Patent: Aug. 13, 2013

(54) PATIENT MONITORING

(75) Inventors: Neil A. Martin, Encino, CA (US); Xiao Hu, Los Angeles, CA (US); Farzad D. Buxey, Marina Del Rey, CA (US); Vesselin Zlatev, Aliso Viejo, CA (US); Monica Sapo, Woodland Hills, CA (US)

(73) Assignees: The Regents of the University of California, Oakland, CA (US); Vesselin Zlatev, Aliso Viejo, CA (US)

( * ) Notice: Subject to any disclaimer, the term of this patent is extended or adjusted under 35 U.S.C. 154(b) by 422 days.

(21) Appl. No.: 12/036,285

(22) Filed: Feb. 24, 2008

(65) Prior Publication Data

US 2009/0216556 A1    Aug. 27, 2009

(51) Int. Cl.
*G06Q 10/00* (2012.01)
*G06Q 50/00* (2012.01)

(52) U.S. Cl.
USPC .................................. 705/2; 705/3; 600/300

(58) Field of Classification Search
USPC .......................................... 705/2–3; 600/300
See application file for complete search history.

(56) References Cited

U.S. PATENT DOCUMENTS

| | | | |
|---|---|---|---|
| 5,553,609 A | 9/1996 | Chen et al. | |
| 5,713,350 A | 2/1998 | Yokota et al. | |
| 5,823,948 A | 10/1998 | Ross, Jr. et al. | |
| 5,827,180 A | 10/1998 | Goodman | |
| 5,832,488 A | 11/1998 | Eberhardt | |
| 5,867,821 A | 2/1999 | Ballantyne et al. | |
| 5,924,074 A | 7/1999 | Evans | |
| 5,950,207 A | 9/1999 | Mortimore et al. | |
| 5,960,403 A | 9/1999 | Brown | |
| 6,049,794 A | 4/2000 | Jacobs et al. | |
| 6,182,029 B1 | 1/2001 | Friedman | |
| 6,226,620 B1 | 5/2001 | Oon | |
| 6,246,992 B1 | 6/2001 | Brown | |
| 6,283,761 B1 | 9/2001 | Joao | |
| 6,375,614 B1 | 4/2002 | Braun et al. | |
| 6,523,009 B1 | 2/2003 | Wilkins | |
| 6,611,846 B1 | 8/2003 | Stoodley | |
| 7,165,221 B2 | 1/2007 | Monteleone et al. | |
| 7,424,679 B1 | 9/2008 | Lamer et al. | |
| 2002/0194029 A1 | 12/2002 | Guan et al. | |

(Continued)

FOREIGN PATENT DOCUMENTS

| | | |
|---|---|---|
| EP | 1102199 A2 | 5/2001 |
| EP | 1587017 A2 | 10/2005 |

OTHER PUBLICATIONS

Knaus WA, Draper EA, Wagner DP, and Zimmerman JE. APACHE II: a severity of disease classification system. Crit Care Med 1985; 13: 818-829.

(Continued)

*Primary Examiner* — Luke Gilligan
(74) *Attorney, Agent, or Firm* — St. Onge Steward Johnston & Reens LLC

(57) ABSTRACT

Some embodiments of the invention provide a method for monitoring patients in a unit of a hospital, an entire hospital, or several hospitals. In some of these embodiments, the methods receives data pertaining to multiple patients. The method aggregates the data and calculated scores based on the received data. The method also calculates trends associated with the aggregated data and/or the generated scores. The method further displays the aggregated and calculated data in a unified display that facilitates efficient allocation of resources in the hospital unit, the hospital, or the group of hospitals.

20 Claims, 20 Drawing Sheets

(56) References Cited

U.S. PATENT DOCUMENTS

| | | |
|---|---|---|
| 2003/0140044 A1 | 7/2003 | Mok et al. |
| 2004/0073453 A1 | 4/2004 | Nenov et al. |
| 2004/0186746 A1 | 9/2004 | Angst et al. |
| 2006/0064020 A1* | 3/2006 | Burnes et al. ............... 600/481 |
| 2006/0071797 A1* | 4/2006 | Rosenfeld et al. ......... 340/573.1 |
| 2007/0005397 A1 | 1/2007 | Lee |
| 2008/0052115 A1 | 2/2008 | Spradley et al. |
| 2008/0214904 A1* | 9/2008 | Saeed et al. ................. 600/301 |
| 2012/0116180 A1* | 5/2012 | Rothman et al. ............. 600/300 |

OTHER PUBLICATIONS

Render ML, Welsh DE, Kollef M, Lott JH, 3rd, Hui S, Weinberger M, Tsevat J, Hayward RA, and Hofer TP. Automated computerized intensive care unit severity of illness measure in the Department of Veterans Affairs: preliminary results. SISVistA Investigators. Scrutiny of ICU Severity Veterans Health Sysyems Technology Architecture. Crit Care Med 2000; 28: 3540-3546.

Junger A, Bottger S, Engel J, Benson M, Michel A, Rohrig R, Jost A, and Hempelmann G. Automatic calculation of a modified APACHE II score using a patient data management system (PDMS). Int J Med Inform 2002; 65: 145-157.

Markgraf R, Deutschinoff G, Pientka L, and Scholten T. Comparison of acute physiology and chronic health evaluations II and III and simplified acute physiology score II: a prospective cohort study evaluating these methods to predict outcome in a German interdisciplinary intensive care unit. Crit Care Med 2000; 28: 26-33.

Fery-Lemonnier E, Landais P, Loirat P, Kleinknecht D, and Brivet F. Evaluation of severity scoring systems in ICUs—translation, conversion and definition ambiguities as a source of inter-observer variability in Apache II, SAPS and OSF. Intensive Care Med 1995; 21: 356-360.

Engel JM, Junger A, Bottger S, Benson M, Michel A, Rohrig R, Jost A, and Hempelmann G. Outcome prediction in a surgical ICU using automatically calculated SAPS II scores. Anaesth Intensive Care 2003; 31: 548-554.

Bion JF, Aitchison TC, Edlin SA, and Ledingham 1M. Sickness scoring and response to treatment as predictors of outcome from critical illness. Intensive Care Med 1988; 14: 167-172.

European Search Report; Application No. EP 09 15 3532; Issued: Sep. 19, 2011; 6 pages.

* cited by examiner

| Patient Name | Admin | MEWS | MEWS Δ | SAPS | SAPS Δ | APACHE II | APACHE II Δ | HR | HR Δ | BP | BP Δ | Glucose | Glucose Δ | Temp | Temp Δ | Resp. Rate | Resp. Rate Δ | AVPU | AVPU Δ | O₂ Sat. | O₂ Sat. Δ | Urine | Urine Δ |
|---|---|---|---|---|---|---|---|---|---|---|---|---|---|---|---|---|---|---|---|---|---|---|---|
| John Doe | | 11 | 4⇑ | 10 | 2⇑ | 20 | 0 | 89 | 3⇑ | 121/81 | 3⇑/1⇑ | 95 | 0 | 98.6 | 0 | 30 | 2⇑ | 0 | 0 | 96 | 0 | 100 | 1⇑ |
| Jane Doe | | 5 | 2⇑ | 11 | 0 | 10 | 0 | 67 | 4⇑ | 111/67 | 2⇑/5⇑ | 77 | 3⇑ | 99 | .3⇑ | 21 | 1⇑ | 1 | 1⇑ | 99 | 0 | 89 | 3⇑ |
| Jim Doe | | 12 | 5⇑ | 15 | 3⇑ | 25 | 3⇑ | 99 | 8⇑ | 139/99 | 3⇑/2⇑ | 101 | 7⇑ | 102 | .1⇑ | 30 | 3⇑ | 2 | 1⇑ | 94 | 1⇑ | 88 | 4⇑ |
| Jean Doe | | 0 | 1⇑ | 1 | 3⇑ | 1 | 2⇑ | 72 | 2⇑ | 100/69 | 0/0 | 75 | 0 | 98.6 | 0 | 9 | 0 | 0 | 0⇑ | 99 | 0 | 100 | 0 |

| Patient Name | Admin | MEWS | MEWS Δ | SAPS | SAPS Δ | APACHE II | APACHE II Δ | HR | HR Δ | BP | BP Δ | Glucose | Glucose Δ | Temp | Temp Δ | Resp. Rate | Resp. Rate Δ | AVPU | AVPU Δ | O₂ Sat. | O₂ Sat. Δ | Urine | Urine Δ |
|---|---|---|---|---|---|---|---|---|---|---|---|---|---|---|---|---|---|---|---|---|---|---|---|
| Jim Doe | | 9 | 5⇑ | 15 | 3⇑ | 25 | 3⇑ | 99 | 8⇑ | 139/99 | 3⇑/2⇑ | 101 | 7⇑ | 102 | .1⇑ | 30 | 3⇑ | 2 | 1⇑ | 94 | 1⇑ | 88 | 4⇑ |
| John Doe | | 8 | 1⇑ | 10 | 2⇑ | 20 | 0 | 89 | 3⇑ | 121/81 | 3⇑/1⇑ | 95 | 0 | 98.6 | 0 | 30 | 2⇑ | 0 | 0 | 96 | 0 | 100 | 1⇑ |
| ... | ... | ... | ... | ... | ... | ... | ... | ... | ... | ... | ... | ... | ... | ... | ... | ... | ... | ... | ... | ... | ... | ... | ... |
| Jane Doe | | 5 | 2⇑ | 11 | 0 | 10 | 0 | 67 | 4⇓ | 111/67 | 2⇓/5⇓ | 77 | 3⇓ | 99 | .3⇓ | 21 | 1⇓ | 1 | 1⇑ | 99 | 0 | 89 | 3⇓ |
| Jean Doe | | 0 | 1⇓ | 1 | 3⇑ | 1 | 2⇑ | 72 | 2⇓ | 100/69 | 0/0 | 75 | 0 | 98.6 | 0 | 9 | 0 | 0 | 0⇓ | 99 | 0 | 100 | 0 |

Figure 3

| Patient Name | Admin | MEWS | MEWS Δ | SAPS | SAPS Δ | APACHE II | APACHE II Δ | HR | HR Δ | BP | BP Δ | Glucose | Glucose Δ | Temp | Temp Δ | Resp. Rate | Resp. Rate Δ | AVPU | AVPU Δ | O₂ Sat. | O₂ Sat. Δ | Urine | Urine Δ |
|---|---|---|---|---|---|---|---|---|---|---|---|---|---|---|---|---|---|---|---|---|---|---|---|
| Jim Doe | | 9 | 5⇑ | 15 | 3⇑ | 25 | 3⇑ | 99 | 8⇑ | 139/99 | 3⇑/2⇑ | 101 | 7⇑ | 38.5 | .1⇑ | 30 | 3⇑ | 2 | 1⇑ | 94 | 1⇑ | 88 | 4⇑ |
| Jane Doe | | 5 | 2⇑ | 11 | 0 | 10 | 0 | 67 | 4⇓ | 111/67 | 2⇓/5⇓ | 77 | 3⇓ | 36.0 | .3⇑ | 21 | 1⇓ | 1 | 1⇑ | 99 | 0 | 89 | 3⇓ |
| ... | ... | ... | ... | ... | ... | ... | ... | ... | ... | ... | ... | ... | ... | ... | ... | ... | ... | ... | ... | ... | ... | ... | ... |
| John Doe | | 8 | 1⇑ | 10 | 2⇑ | 20 | 0 | 89 | 3⇑ | 121/81 | 3⇑/1⇑ | 95 | 0 | 35.1 | 0 | 30 | 2⇑ | 0 | 0 | 96 | 0 | 100 | 1⇑ |
| Jean Doe | | 0 | 1⇓ | 1 | 3⇑ | 1 | 2⇑ | 72 | 2⇓ | 100/69 | 0/0 | 75 | 0 | 35.5 | 0 | 9 | 0 | 0 | 0⇓ | 99 | 0 | 100 | 0 |

Figure 12

| Patient Name | Admin | MEWS | MEWS Δ | SAPS | SAPS Δ | APACHE II | APACHE II Δ | HR | HR Δ | BP | BP Δ | Glucose | Glucose Δ | Temp | Temp Δ | Resp. Rate | Resp. Rate Δ | AVPU | AVPU Δ | O₂ Sat. | O₂ Sat. Δ | Urine | Urine Δ |
|---|---|---|---|---|---|---|---|---|---|---|---|---|---|---|---|---|---|---|---|---|---|---|---|
| Jim Doe | | 9 | 5⇑ | 15 | 3⇑ | 25 | 3⇑ | 99 | 8⇑ | 139/99 | 3⇑/2⇑ | 101 | 7⇑ | 102 | .1⇑ | 30 | 3⇑ | 2 | 1⇑ | 94 | 1⇓ | 88 | 4⇓ |
| John Doe | | 8 | 1⇓ | 10 | 2⇑ | 20 | 0 | 89 | 3⇑ | 121/81 | 3⇑/1⇑ | 95 | 0 | 98.6 | 0 | 30 | 2⇑ | 0 | 0 | 96 | 0 | 100 | 1⇑ |
| ... | ... | ... | ... | ... | ... | ... | ... | ... | ... | ... | ... | ... | ... | ... | ... | ... | ... | ... | ... | ... | ... | ... | ... |
| Jane Doe | | 5 | 2⇑ | 11 | 0 | 10 | 0 | 67 | 4⇓ | 111/67 | 2⇑/5⇑ | 77 | 3⇑ | 99 | .3⇑ | 21 | 1⇑ | 1 | 1⇑ | 99 | 0 | 89 | 3⇓ |
| Jean Doe | | 0 | 1⇑ | 1 | 3⇑ | 1 | 2⇑ | 72 | 2⇑ | 100/69 | 0/0 | 75 | 0 | 98.6 | 0 | 9 | 0 | 0 | 0⇑ | 99 | 0 | 100 | 1⇑ |

Figure 13

| Patient Name | Admin | MEWS | MEWS Δ | SAPS | SAPS Δ | APACHE II | APACHE II Δ | HR | HR Δ | BP | BP Δ | Glucose | Glucose Δ | Temp | Temp Δ | Resp. Rate | Resp. Rate Δ | AVPU | AVPU Δ | O₂ Sat. | O₂ Sat. Δ | Urine | Urine Δ |
|---|---|---|---|---|---|---|---|---|---|---|---|---|---|---|---|---|---|---|---|---|---|---|---|
| Jim Doe | | 9 | 5⇑ | 15 | 3⇑ | 25 | 3⇑ | 99 | 8⇑ | 139/99 | 3⇑/2⇑ | 101 | 7⇑ | 102 | .1⇑ | 30 | 3⇑ | 2 | 1⇑ | 94 | 1⇓ | 88 | 4⇓ |
| John Doe | | 8 | 1⇓ | 10 | 2⇑ | 20 | 0 | 89 | 3⇑ | 121/81 | 3⇑/1⇑ | 95 | 0 | 98.6 | 0 | 30 | 2⇑ | 0 | 0 | 96 | 0 | 100 | 1⇑ |
| ... | ... | ... | ... | ... | ... | ... | ... | ... | ... | ... | ... | ... | ... | ... | ... | ... | ... | ... | ... | ... | ... | ... | ... |
| Jane Doe | | 5 | 2⇑ | 11 | 0 | 10 | 0 | 67 | 4⇓ | 111/67 | 2⇑/5⇑ | 77 | 3⇑ | 99 | .3⇑ | 21 | 1⇑ | 1 | 1⇑ | 99 | 0 | 89 | 3⇓ |

Figure 14

| Patient Name | Admin | MEWS | MEWS Δ | SAPS | SAPS Δ | APACHE II | APACHE II Δ | HR | HR Δ | BP | BP Δ | Glucose | Glucose Δ | Temp | Temp Δ | Resp. Rate | Resp. Rate Δ | AVPU | AVPU Δ | O₂ Sat. | O₂ Sat. Δ | Urine | Urine Δ |
|---|---|---|---|---|---|---|---|---|---|---|---|---|---|---|---|---|---|---|---|---|---|---|---|
| Jim Doe |  | 9 | 5⇑ | 15 | 3⇑ | 25 | 3⇑ | 99 | 8⇑ | 139/99 | 30/20 | 101 | 7⇑ | 102 | .1⇑ | 30 | 3⇑ | 2 | 1⇑ | 94 | 1⇓ | 88 | 4⇓ |
| Jane Doe |  | 5 | 2⇑ | 11 | 0 | 10 | 0 | 67 | 4⇓ | 111/67 | 2/50 | 77 | 3⇑ | 99 | .3⇑ | 21 | 1⇑ | 1 | 1⇑ | 99 | 0 | 89 | 3⇑ |
| ... | ... | ... | ... | ... | ... | ... | ... | ... | ... | ... | ... | ... | ... | ... | ... | ... | ... | ... | ... | ... | ... | ... | ... |
| John Doe |  | 8 | 1⇑ | 10 | 2⇑ | 20 | 0 | 89 | 3⇑ | 121/81 | 3⇑/1⇑ | 95 | 0 | 98.6 | 0 | 30 | 2⇑ | 0 | 0 | 96 | 0 | 100 | 1⇑ |
| Jean Doe |  | 0 | 1⇑ | 1 | 3⇑ | 1 | 2⇑ | 72 | 2⇓ | 100/69 | 0/0 | 75 | 0 | 98.6 | 0 | 9 | 0 | 0 | 0⇑ | 99 | 0 | 100 | 0 |

| Patient Name | Admin | MEWS | MEWS Δ | SAPS | SAPS Δ | APACHE II | APACHE II Δ | HR | HR Δ | BP | BP Δ | Glucose | Glucose Δ | Temp | Temp Δ | Resp. Rate | Resp. Rate Δ | AVPU | AVPU Δ | O₂ Sat. | O₂ Sat. Δ | Urine | Urine Δ |
|---|---|---|---|---|---|---|---|---|---|---|---|---|---|---|---|---|---|---|---|---|---|---|---|
| Jane Doe |  | 5 | 2⇑ | 11 | 0 | 10 | 0 | 67 | 4⇓ | 111/67 | 2/50 | 77 | 3⇑ | 99 | .3⇑ | 21 | 1⇑ | 1 | 1⇑ | 99 | 0 | 89 | 3⇑ |
| Jim Doe |  | 9 | 5⇑ | 15 | 3⇑ | 25 | 3⇑ | 99 | 8⇑ | 139/99 | 3⇑/2⇑ | 101 | 7⇑ | 102 | .1⇑ | 30 | 3⇑ | 2 | 1⇑ | 94 | 1⇓ | 88 | 4⇓ |
| ... | ... | ... | ... | ... | ... | ... | ... | ... | ... | ... | ... | ... | ... | ... | ... | ... | ... | ... | ... | ... | ... | ... | ... |
| John Doe |  | 8 | 1⇑ | 10 | 2⇑ | 20 | 0 | 89 | 3⇑ | 121/81 | 3⇑/1⇑ | 95 | 0 | 98.6 | 0 | 30 | 2⇑ | 0 | 0 | 96 | 0 | 100 | 1⇑ |
| Jean Doe |  | 0 | 1⇑ | 1 | 3⇑ | 1 | 2⇑ | 72 | 2⇓ | 100/69 | 0/0 | 75 | 0 | 98.6 | 0 | 9 | 0 | 0 | 0⇑ | 99 | 0 | 100 | 0 |

1500 / 1505

1600

| Patient Name | Admin | MEWS | MEWS Δ | SAPS | SAPS Δ | APACHE II | APACHE II Δ | Glucose | Glucose Δ |
|---|---|---|---|---|---|---|---|---|---|
| John Doe |  | 11 | 1⇓ | 10 | 2⇓ | 20 | 0 | 95 | 0 |
| Jane Doe |  | 5 | 2⇑ | 11 | 0 | 10 | 0 | 77 | 3⇓ |
| Jim Doe |  | 12 | 5⇑ | 15 | 3⇑ | 25 | 3⇑ | 101 | 7⇑ |
| Jean Doe |  | 0 | 1⇓ | 1 | 3⇓ | 1 | 2⇓ | 75 | 0 |

| 130 Patient Name | HR | HR Δ | Sub Δ | Sub |
|---|---|---|---|---|
| Jane Doe | 67 | 4⇓ | 0 | 0 |

1805

| MEWS | MEWS Δ |
|---|---|
| 5 | 2⇑ |

1810

| Temp | Temp Δ | Sub | Sub Δ |
|---|---|---|---|
| 36.0 | .3⇑ | 0 | 0 |

| AVPU | AVPU Δ | Sub | Sub Δ |
|---|---|---|---|
| 3 | 3⇑ | 3 | 3⇑ |

1820 Add sub-scores together.

| Resp. Rate | Resp. Rate Δ | Sub | Sub Δ |
|---|---|---|---|
| 29 | 1⇑ | 2 | 1⇑ |

| BP | BP Δ | Sub | Sub Δ |
|---|---|---|---|
| 111 | 2⇑ | 0 | 0 |

It appears the patient has suffered kidney failure. Would you like to view information regarding this condition?

Yes   No

*Figure 23*

| MEWS Elements | 3 | 2 | 1 | 0 | 1 | 2 | 3 |
|---|---|---|---|---|---|---|---|
| Blood Pressure | <70 | 71-80 | 81-100 | 101-199 | | >=200 | |
| Heart Rate | | <40 | 41-50 | 51-100 | 101-110 | 111-129 | >=130 |
| Respiratory Rate | | <9 | | 9-14 | 15-20 | 21-29 | >=30 |
| Temperature | | <35 | | 35-38.4 | | 38.5 | |
| AVPU Score | | | | A<sub>lert</sub> | Reacting to V<sub>oice</sub> | Reacting to P<sub>ain</sub> | U<sub>nresponsive</sub> |

*Figure 19*

PATIENT MONITORING

FIELD OF THE INVENTION

The invention relates to the field of health care. More specifically, the invention relates to systems and methods for monitoring patients throughout a hospital or hospital chain.

BACKGROUND OF THE INVENTION

The quality of health care is constantly evolving and improving as new less invasive surgical techniques, more effective medications, and better methods of treatment are constantly being discovered and invented. Improvements in health care have also occurred through better use and management of patient information. One such use has allowed medical personnel to reliably predict future probable conditions of a patient through trend analysis of the patient's information. Trends within various patient vital signs (e.g., blood pressure, heart rate, body temperature, etc.) have been shown to reliably indicate future medical conditions or complications.

Attempts have been made to create a standard or objective way to measure trends in a patient's condition by quantifying the results of such trends into one or more "severity scores". Severity scores are usually developed by combined efforts from multiple healthcare organizations. Such efforts have the primary aim of quantifying patient illness such that mortality of an organization can be adjusted by considering the expected survival rate based on these severity scores as well as providing a reliable prognosis of probable changes in the condition of the patient. The severity scores thus assist in providing a quicker response to treat any such changes.

To be an objective measure requires that severity scores should be defined using patient information that may include laboratory test results, vital signs, etc. To achieve consistent scoring requires that definitions of severity scores should be clearly specified so that the processes used in the mapping of the vital signs to the severity score are enumerated.

Many studies have been done on validating existing severity scoring metrics. Severity scores such as Acute Physiology and Chronic Health Examination (APACHE) and Simplified Acute Physiology Score (SAPS) have been well known for purposes including mortality prediction and patient stratification. Other scores, such as the Modified Early Warning Score (MEWS), have been proposed for early detection of patient deterioration and have been validated in several pilot studies. However, the impact of these severity scores into daily clinical practice remains elusive because these severity scores have not been widely accepted and integrated into typical workflows of patient care for possible reasons including lack of an automated scoring system, ambiguities in terms of specification of data collection protocol for scoring, and lack of studies of applying severity scores to individual patients. More specifically, the barriers to the adoption of such severity scores include insufficient data gathering, time alignment issues resulting from inconsistent data gathering, and improper data processing (e.g., aggregation and unit conversion) as some examples.

Typically, the data reporting for such severity scoring is conducted on a manual basis by some medical personnel assigned the task to gather and aggregate such data. As a result, the reporting is at times inconsistent or subjective. Additionally, trend analysis may not include sufficient diversity of patients to accurately predict the probable outcome for all cases. For example, it is not clear whether the various existing scoring metrics can perform multiple scoring over larger sets of data points and whether or not the various existing scoring metrics can track temporal score changes.

Additional deficiencies in current severity scoring result from the delay associated with the data gathering and analysis. For instance, the existing scoring metrics only take recorded data after it has been manually transcribed from some vital sign monitor into a database. The time it takes for the data gathering to be completed and further still for the trend analysis to be completed can cause sufficient delay which reduces or defeats the effectiveness and potential early warning provided by the severity score.

The penetration of information technology (IT) into the various aspects of health care has assisted to alleviate some of the data gathering and data management overhead previously associated with providing health care. Establishment and wide adoption of industry-wide standards such as Health Level Seven (HL7) and Digital Imaging and Communications in Medicine (DICOM) together with the much improved computational capability, data storage capability, and fast communication platforms, have provided an ideal environment for the further development of more dedicated IT solutions tailored for more specific clinical challenges.

However, there is a need to better leverage information stored and managed by these IT resources to provide improved health care services to patients. Specifically, there is a need for a severity scoring system that is: (1) highly automated, (2) supports the computation of multiple scores simultaneously, and (3) supports both retrospective and online (i.e., real-time) modes of operation.

There is also a need to cut costs and better prioritize patient care. Hospitals generally have different units according to the level of monitoring and care provided to patients in the unit. Intensive care units (ICUs) provide the most monitoring to a patient, as there is often a one-to-one patient-to-nurse ratio. General wards provide the least amount of monitoring in a hospital. Intermediary "step-down" units provide less monitoring than an ICU, but more than a general ward. Substantial cost-savings are achieved when a patient is discharged from a unit with higher monitoring and moved to a unit with lower monitoring (or discharged from a hospital altogether). These cost savings can amount to thousands of dollars or more per day per bed vacated in an ICU. This cost may include fees of an intensivist—a specialized doctor who oversees an ICU. Because intensivists are relatively rare (approximately 1,200 intensivists compared to 5,000 hospitals in the United States), intensivists often oversee ICUs of several hospitals at once. Discharging a patient from an ICU would thusly result in both a substantial cost savings and an increase in the availability of intensivists.

The current practice of prioritizing patient care is time-consuming and inefficient, and may cause unnecessary delay in discharging a patient. Generally, medical interns perform daily "pre-rounds." This consists of manually retrieving raw data for individual patients from various hospital systems. Interns create summaries, called rounding lists, for an attending physician to read through and make a determination regarding prioritizing the care of the patients on the list. Performing pre-rounds and generating rounding lists can often take upwards of one hour. Furthermore, the attending physician is relied upon to expend time and expertise in prioritizing the patients. Patients who are good candidates for discharge from a unit are often not discharged in a timely fashion because teams responsible for discharging patients are not privy to a real-time snapshot of the patient's condition. Furthermore, doctors' time is used in an inefficient manner in generating and evaluating rounding lists.

Therefore, there is a need in the art for methods and systems that enable healthcare providers to better monitor patients.

SUMMARY OF THE INVENTION

Some embodiments of the invention provide a method for monitoring patients in one or more units of a hospital, an entire hospital, or several hospitals. In some of these embodiments, the method receives data pertaining to multiple patients. The method aggregates the data and calculates scores based on the received data. The method also calculates trends associated with the aggregated data and/or the generated scores. The method further displays the aggregated and calculated data in a unified display that facilitates efficient allocation of resources in the hospital unit, the hospital, or the group of hospitals.

In some embodiments, the unified display is a list. In some embodiments, the list displays severity scores and trends associated with the severity scores. The list also displays patient names in addition to the severity scores and trends, where a trend (also called a "delta") is a change in a piece of recorded data or a calculated score over a time period. The list allows for sorting based on severity score and trend. In some embodiments, the list displays objective or subjective recorded health data (e.g., vitals, such as blood pressure, heart rate, AVPU score, etc.). Some embodiments provide the list in a graphical user interface (GUI). In some embodiments, a user of the GUI may view detailed information regarding a recorded data value, a severity score, or a trend by selecting (e.g., clicking) the recorded data value, the score, or the trend. In some embodiments, the list is first unsorted and a user request specifies a particular sorting of the list. In other embodiments, the list is first unsorted and a configuration setting specifies a particular sorting of the list. In some such embodiments, the configuration setting specifies a stored user request that previously specified a particular sorting of the list.

Some embodiments detect that a patient is suffering from a certain medical condition and display a GUI with more detailed information regarding the medical condition. In some embodiments, this more detailed information entails symptoms and treatment information.

Some embodiments of the invention provide a process for generating an alarm when a patient's health is deteriorating. In some embodiments, the alarm is generated in response to (1) a severity score and a trend of the severity score, (2) a recorded data value (e.g., a vital sign) and of the recorded data value, and/or (3) a combination of a recorded data value, severity score, and their trends. Such a condition is automatically detected when the scores, recorded data values (e.g., vital signs), and/or trends meet or exceed a certain threshold. Some embodiments perform the alerting (i.e., generate the alarms) in real time.

BRIEF DESCRIPTION OF THE DRAWINGS

The novel features of the invention are set forth in the appended claims. However, for purpose of explanation, several embodiments of the invention are set forth in the following figures.

FIG. 1 illustrates an embodiment of a patient list that displays patients, severity scores, recorded data, and trends.

FIG. 2 illustrates an embodiment of a patient list that displays patients, severity scores, recorded data, and trends that has been sorted by a severity score.

FIG. 3 illustrates an embodiment of a patient list that displays patients, severity scores, recorded data, and trends that has been sorted by a severity score trend.

FIG. 12 illustrates an embodiment of a patient list that displays patients, severity scores, recorded data, and trends that has been sorted by glucose level.

FIG. 13 illustrates an embodiment of a patient list that displays patients, severity scores, recorded data, and trends that has been sorted by glucose level trend.

FIG. 14 illustrates an embodiment of a patient list that displays patients, severity scores, recorded data, and trends that has been sorted by temperature.

FIG. 15 illustrates an embodiment of a patient list that displays patients, severity scores, recorded data, and trends that has been sorted by temperature trend.

FIG. 16 illustrates an embodiment of a customized patient list.

FIG. 18 illustrates an example of a drill-down view in accordance with some embodiments.

FIG. 19 shows a scoring algorithm for MEWS severity scores.

FIG. 23 illustrates a prompt offering to display more detailed information about an automatically detected condition in accordance with some embodiments.

DETAILED DESCRIPTION OF THE INVENTION

Figure 4:
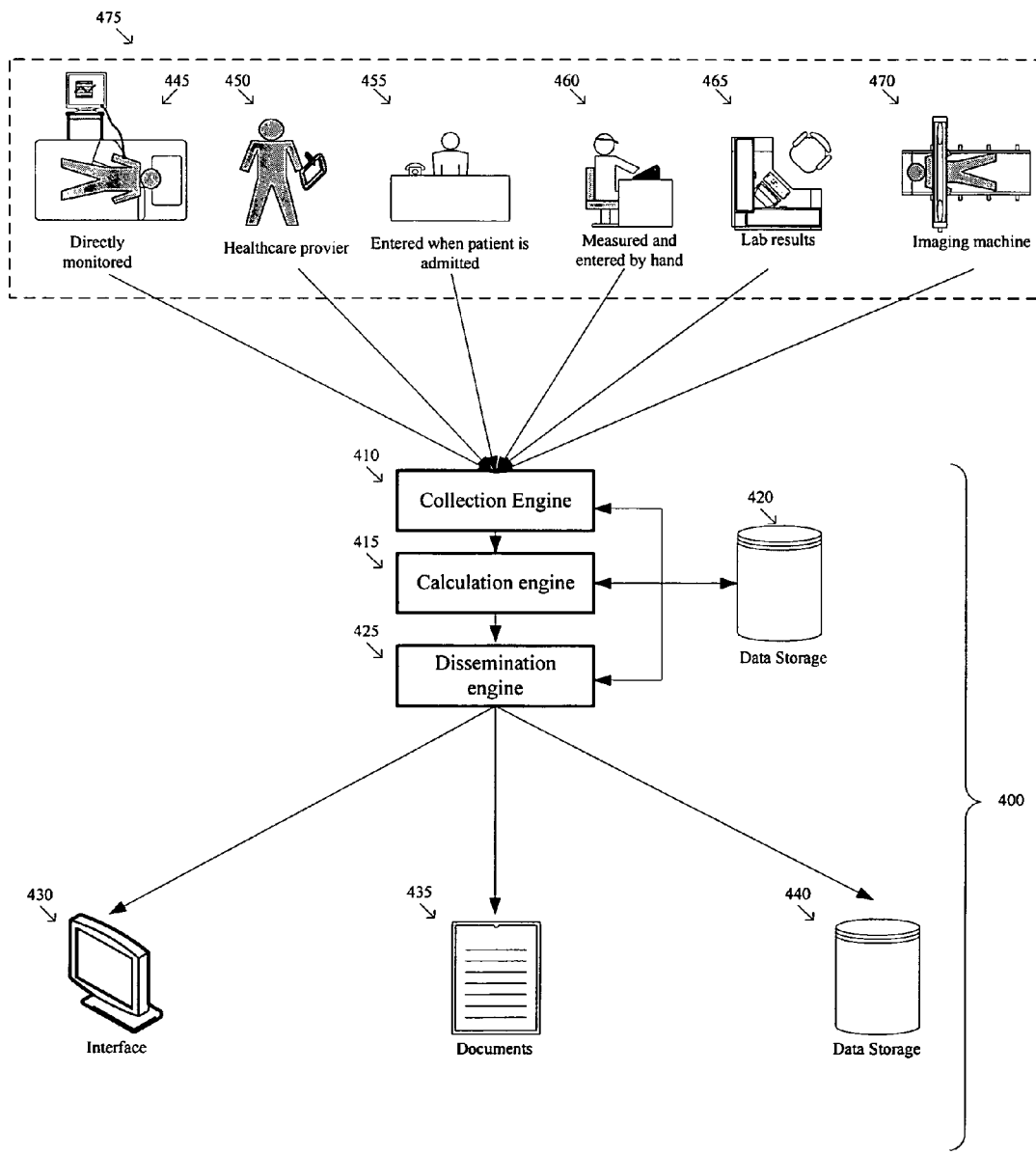
FIG. 4 illustrates an embodiment of a hospital-wide system that collects data pertaining to several patients and reports the data to several interfaces.

In the following description, numerous details are set forth for purpose of explanation. However, one of ordinary skill in the art will realize that the invention may be practiced without the use of these specific details. For instance, well-known structures and devices are shown in block diagram form in order not to obscure the description of the invention with unnecessary detail.

I. Overview

Some embodiments of the invention provide a method for monitoring patients in a unit of a hospital, an entire hospital, or several hospitals. In some of these embodiments, the method receives recorded data pertaining to multiple patients. In some embodiments, the method calculates scores based on the received data. The method also calculates trends associated with the aggregated data and/or the generated scores, where a trend (also called a "delta") is a change in a piece of recorded data or a calculated score over a time period. The method aggregates the received and calculated data into a list. The method further displays the aggregated and calculated data in a unified display that facilitates efficient allocation of resources in the hospital unit, the hospital, or the group of hospitals.

In some embodiments, the unified display is a list. FIG. 1 illustrates an example of such a list 100. The list 100 includes records for several patients. In this example, each patient's record is shown as a row in the list. In the list 100, each column displays a value containing certain information about the patient. These columns include a name column 110, one or more administrative data column 115, several severity score columns 120, and recorded data columns 125. The name column 110 shows the name of each patient, while the administrative data column 115 displays administrative data, which can include information such as location, patient ID number, or other information. Severity score column group 120 contains columns that list several types of severity score, such as MEWS, APACHE II, and SAPS II. Recorded data column group 125 contains columns that display recorded patient data. These column groups 120 and 125 also include columns that show trends of recorded patient data.

The list 100 is sortable by any of the columns in order to allow efficient prioritization of health care and to facilitate discharging of patients. FIG. 2 shows a patient list 200, which is the patient list 100 from FIG. 1 sorted by MEWS severity score. FIG. 3 shows a patient list 300 that is sorted by trend of MEWS severity score. The sorting aids in efficiently prioritizing patient care in several ways.

For instance, a doctor making rounds can use the sorted list to determine which patients he should visit first. Teams monitoring specific recorded data (e.g. a hyperglycemia team that oversees glucose levels in patients) also receive a fast, at-a-glance overview of all patients for whom the team is responsible. Based on this quick review, such teams can prioritize patients to examine. In addition, a team (e.g., a bed control team or a discharge team) can use the sorted list to quickly determine that a patient can be discharged from a unit of a hospital.

Based on severity scores, recorded patient data, and/or calculated trends, the monitoring method of some embodiments also generates alerts. Such alerts can be used to quickly address a patient condition. For instance, such alerts enable a rapid response team to predict or quickly respond to a patient episode requiring attention.

The list 100 is described above with a particular set of data recordings, scores, features, and layout. One skilled in the art would realize, however, that other embodiments might implement such a list with a different set of recordings, scores, features, and layout.

II. System Architecture

FIG. 4 illustrates a clinical information system (CIS) 400 that implements the above-described patient monitoring methodology in some embodiments. Specifically, the clinical information system 400 aggregates and reports data for multiple patients from multiple sources. These sources include directly monitored vital signs recorded by sensors 445 (e.g., heart rate), data entered when a patient is admitted 455, data entered by a healthcare provider 450 after admittance, data measured and recorded manually (e.g., on a patient's chart) 460, results provided by a lab 465, data from an imaging machine 470, or other sources. As further described below, the patient data can be supplied from one or more units of a hospital 475, from the entire hospital 475, or from several hospitals 475. In this context, a unit of a hospital can be a physical unit (e.g., an intensive control unit, an intermediary step-down unit, a general ward, etc.), or a conceptual service unit relating to a patient condition (e.g., heart attacks, brain strokes, high blood pressure, etc.) serviced by the hospital.

The clinical information system 400 has a collection engine 410, a calculation engine 415, a data storage 420, a dissemination engine 425, and multiple data recipients 430, 435, and 440. The collection engine 410 receives data for multiple patients. The collection engine 410 stores the received data in the data storage 420 after cleansing and normalizing the received data to transform it into a format for storing in the data storage 420. From the cleansed and normalized data, the calculation engine 415 calculates severity scores and trends relating to both the received data and the severity scores, and stores the calculated values in the data storage 420.

The dissemination engine 425 distributes the collected and calculated data. The clinical information system 400 includes multiple different types of data recipients that receive the data from the dissemination engine 425 in some embodiments. Examples of such data recipients include devices 430, such as personal computers, tablet PCs, laptop computers, handheld devices, medical monitoring equipments, and/or other type of electronic devices. The dissemination engine 425 can also distribute physical or electronic documents 435 (e.g., printouts, such as a rounding list or other printed report, or electronic messages, such as XML documents, alert messages, etc.). Lastly, a data recipient can also be a data storage 440 that stores the disseminated data for subsequent review and processing.

The dissemination engine 425 distributes the collected and calculated data differently for different data recipients. For instance, in some embodiments, the dissemination engine is a query manager for the data storage 420 for allowing users of devices 430 to query the data storage 420 by submitting query parameters through the user interface of the devices 430. Such query parameters can be supplied by the devices 430 automatically (e.g., when a user opens a client application of the CIS 400 on a device 430, or makes a selection on this application). Alternatively, these parameters can be supplied manually by a user through the user interface of a device 430.

In some embodiments, the dissemination engine 425 disseminates reports regarding the collected and calculated data in an automated manner. This automated operation can result in the generation and distribution of physical or electronic documents. This operation can occur based on batch processing or real-time processing.

Figure 5:
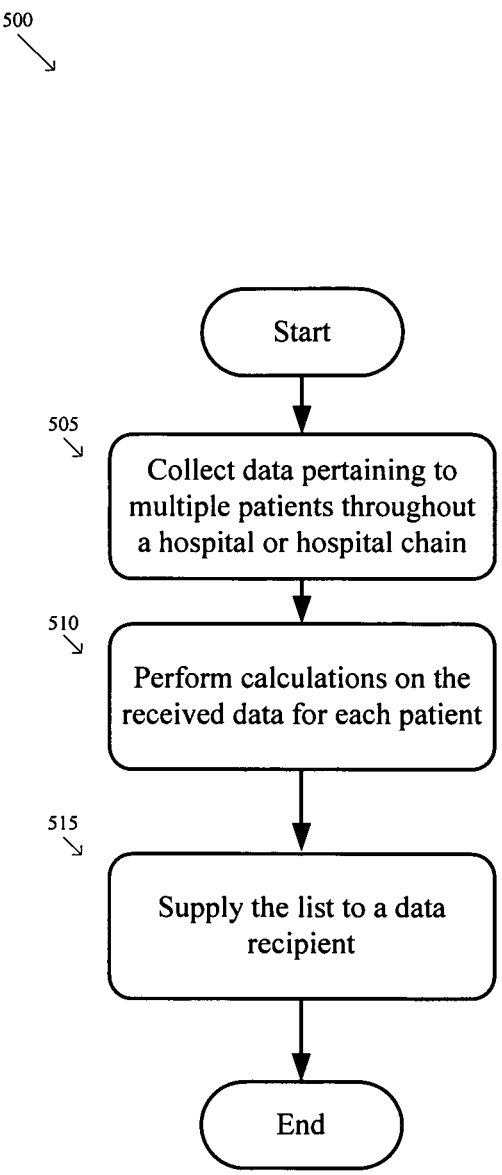
FIG. 5 illustrates a method that receives information from multiple patients and supplies the data to an interface in accordance with some embodiments of the invention.

FIG. 5 provides a conceptual illustration of a process 500 performed by components of the clinical information system 400 of some embodiments. Some embodiments iteratively perform the process 500 to monitor several patients. Even though this process is described in terms of a number of discrete operations performed sequentially, one skilled in the art will understand that this is a conceptual illustration. In other words, the illustrated operations can be implemented differently in different embodiments. In some embodiments, the process 500 is performed at regular time intervals.

As shown in FIG. 5, the process 500 initially starts by collecting (at 505) data pertaining to multiple patients at the collection engine 410. In some embodiments, the data contains objective medical signs (such as blood pressure, heart rate, temperature, respiratory rate, oxygen saturation, blood pressure, urine output, and/or glucose level) and subjective medical signs (such as AVPU score, i.e., Alert, reacting to Voice, reacting to Pain, Unresponsive). At 505, the process cleanses and normalizes this data, and stores this data in the data store 420.

The process then performs (at 510) calculations based on the received data at the calculation engine 415. In some embodiments, the calculation yields a severity score, such as Modified Early Warning Score ("MEWS"), Acute Physiology and Chronic Health Evaluation II ("APACHE II"), or Simplified Acute Physiology Score ("SAPS II"). The process also calculates (at 510) trends of individual medical statistics in the data in some embodiments. One such trend is a difference, a delta ("Δ"), or change over time, between a current value for a health statistic (e.g., severity score or recorded data value) and a baseline value (e.g., at least one preceding value such as the immediately received value, or an average of the previously received values) for the same health statistic. For example, if a current value for heart rate is x and the immediately preceding value for heart rate is y, then the delta (Δ) is (x-y). A delta (Δ) may also be calculated for a severity score. A delta (Δ) value may be an integer, a float, or any other number type.

In some embodiments, the baseline value for a particular health statistic (e.g., a vital or a score) is an average value (e.g., a mean, median, mode, or an average value that discounts the effect of outliers and/or spikes, etc.), minimum value, or maximum value of the recorded value or generated scores over a duration of time (e.g., over a minute, an hour, several hours, a day, or several days). In yet other embodiments, the delta (Δ) is a current rate of change of an average of values received over a period of time. In some embodiments, the method for calculating the delta (Δ) is also user-customizable. In lieu of, or in addition to, a delta (Δ), some embodiments display an average of a health statistic over a period of time. The various periods of time are user-customizable in some embodiments.

Calculation of a severity score itself is discussed in detail in concurrently filed U.S. application Ser. No. 12/036,265, entitled "Multi-Automated Severity Scoring,", which is hereby incorporated into the current application by reference. In some embodiments, calculated values are also stored in the same data structure as the collected patient data, while other embodiments store these values in separate data storages (e.g., separate databases). In conjunction with calculating a delta (A), some embodiments calculate a score to quantify rate of change of the received data values (e.g., vital signs), severity scores, trends, or average values. Other embodiments compute other types of scores to quantify changes in received values, severity scores, and trends.

The process stores (at 510) each calculated data value in the data storage 420. At 515, the process then disseminates or is ready to disseminate the stored recorded and calculated values to one or more data recipients. For instance, in some cases, the process generates a list (like list 100 of FIG. 1) of some or all the patients. As mentioned above, this list might be generated and disseminated automatically by the dissemination engine 425, or it might be generated and disseminated upon receiving a query request from a data recipient.

The data recipient may be a client application or browser of a device 430, may be a recipient of a physical or electronic document 435 generated by the dissemination engine 425, and/or may be a data storage 440 for querying at a later time. In some embodiments, the data recipient receives or displays only a portion of the supplied data. After 515, the process ends.

As mentioned above, the process 500 in some embodiments is performed at regular time intervals (e.g., once a day, once every hour, once every minute, etc.) as a batch process for a single patient and/or multiple patients in one or more units of a hospital, in the entire hospital, or in several hospitals. In other embodiments, the process 500 is performed in real time, where a change in a patient's condition is propagated through the system 400 in real time.

Figure 6:
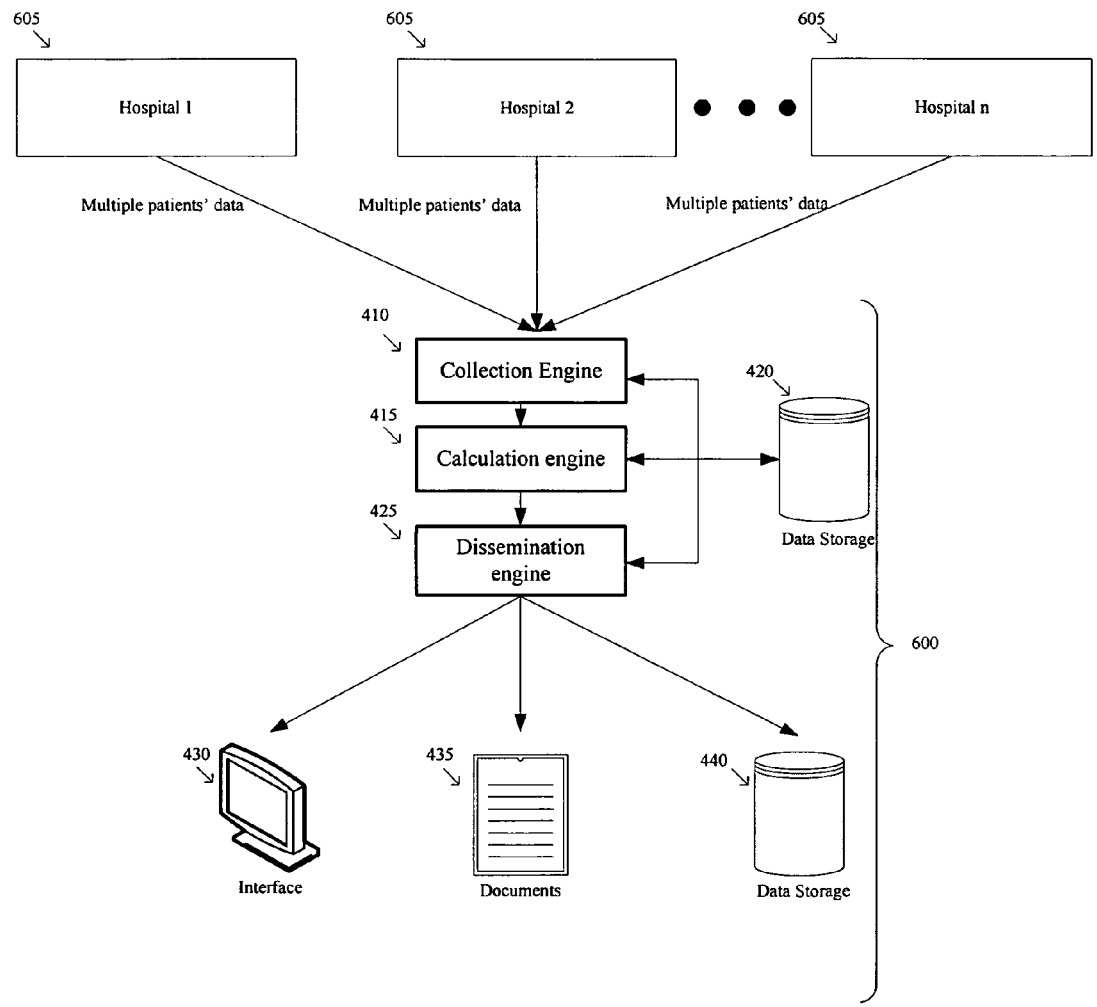
FIG. 6 illustrates an embodiment of a hospital chain-wide monitoring system that aggregates patient data from several hospitals and supplies the data to an interface.
Figure 7:
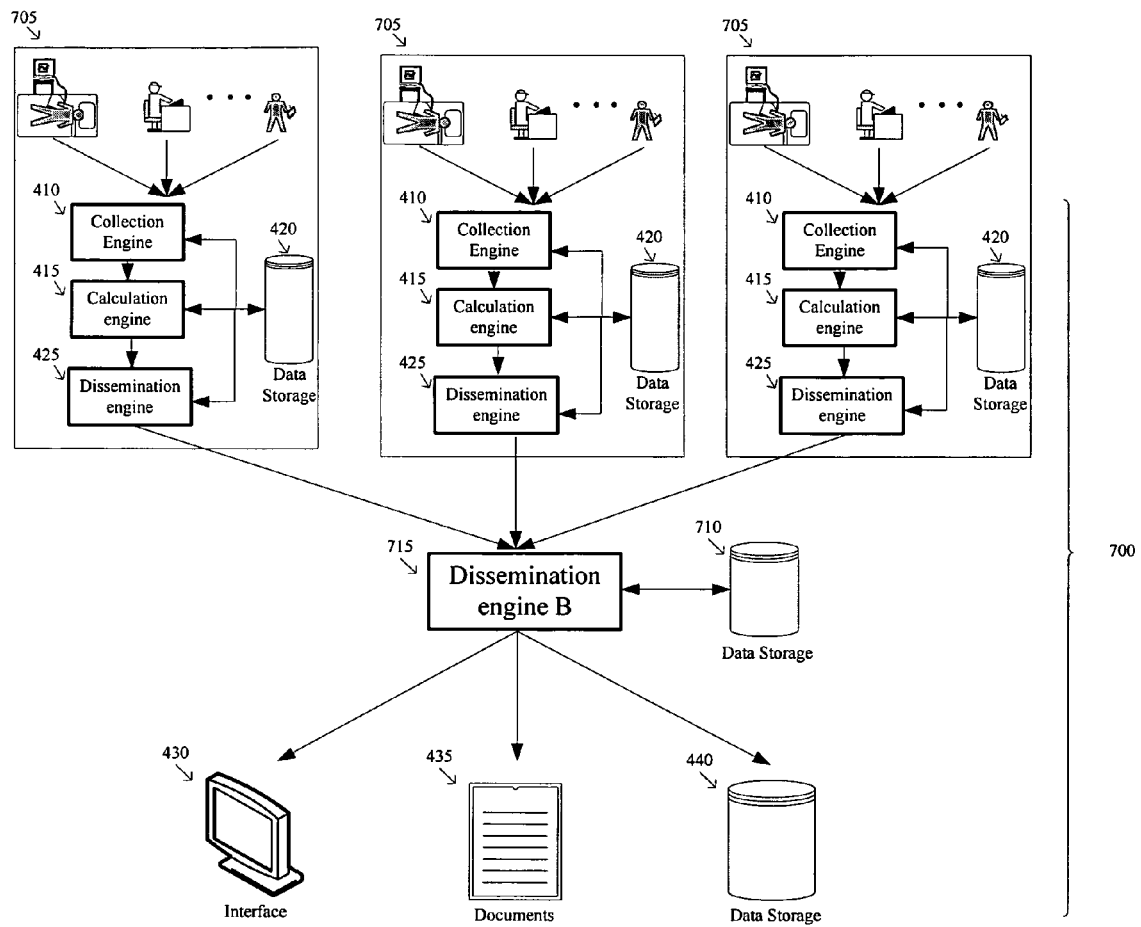
FIG. 7 illustrates an alternate embodiment of a hospital chain-wide monitoring system that aggregates patient data from several hospitals and supplies the data to an interface.

As mentioned above, the clinical information system 400 can monitor patients in one or more units of a hospital, in the entire hospital, or in several hospitals. The architecture of the system may be different for different deployments of the system 400 (e.g., might be for a deployment for one hospital or for several hospitals). FIGS. 6 and 7 illustrate two different architectures. In FIG. 6, clinical information system 600 uses one set of clinical management components (i.e., one set of collection, calculation, and dissemination engines) to monitor patients at several hospitals. All these components can be housed at one location (e.g., one hospital) or multiple locations (e.g., multiple hospitals).

In FIG. 7, on the other hand, the clinical information system 700 has one set of clinical management components (i.e., collection, calculation, and dissemination engines) at each hospital 705. It also includes a dissemination engine 720 that collects data from the dissemination engine 715 of the hospitals, stores this information at an external data store 710, and supplies the received data to data recipients 430, 435, and 440. While FIGS. 4, 6, and 7 illustrate exemplary conceptual architectures of monitoring systems for patient monitoring in one or more units of one or more hospitals, one skilled in the art would recognize that other architectures are possible to achieve the utility discussed above. Moreover, even though several patient lists were described above by reference to FIGS. 1-3, one of ordinary skill will realize that other embodiments might organize the unified display of patient data differently.

III. Clinical Information System

A. Clinical Information System Application User Interface

Some embodiments of the invention provide patient data to users through one or more dashboards. Several examples of dashboards will now be described. In some embodiments, a dashboard is a collection of window panes, with each window pane providing one or more views of a set of patient data (e.g., vitals, severity scores, etc.).

Figure 8:
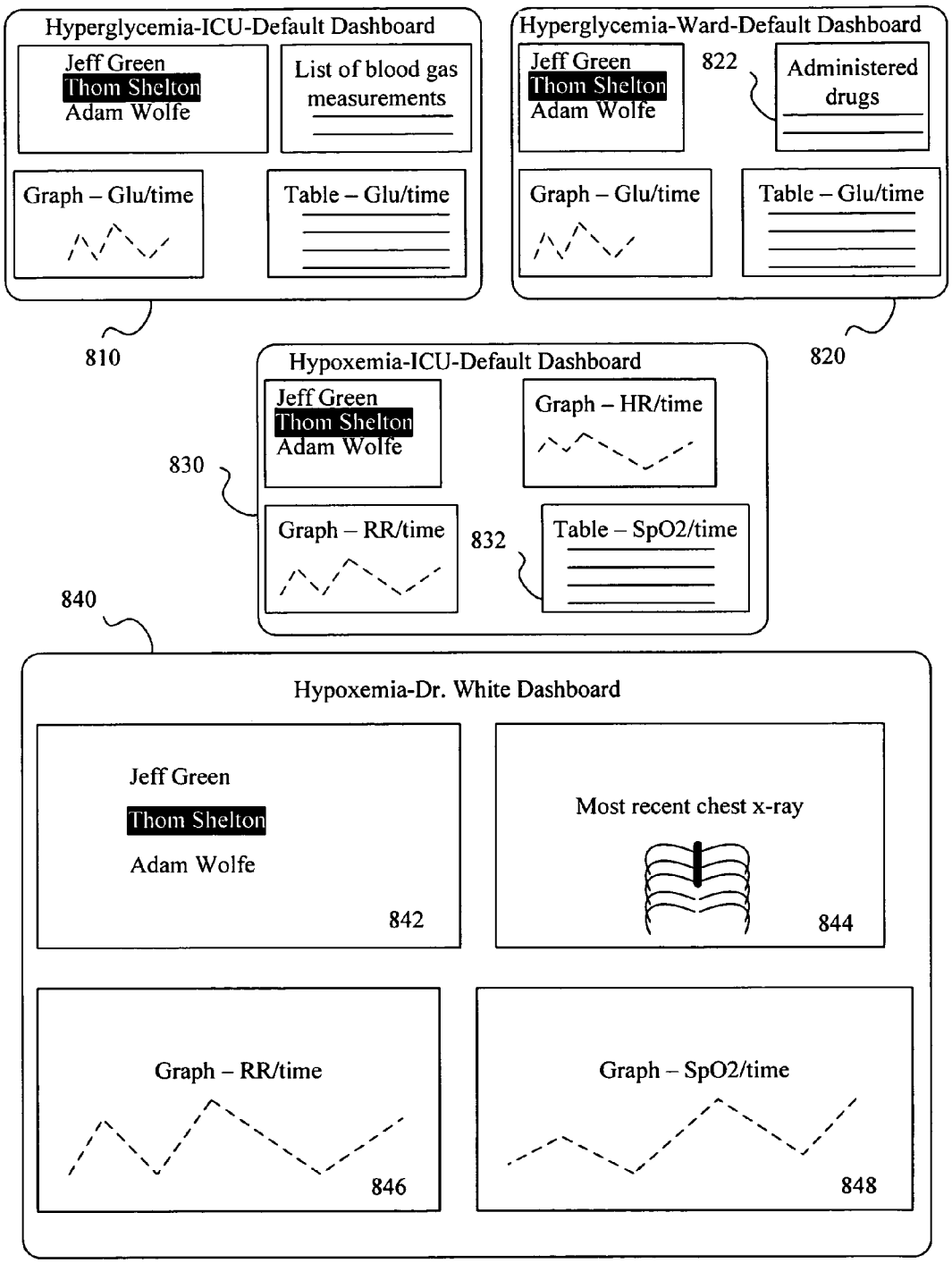
FIG. 8 illustrates four different dashboards.

FIG. 8 illustrates four examples of different dashboards 810-840. Dashboards can be displayed on a variety of interface devices in a variety of embodiments, e.g. computer displays, PDAs, cell phones, etc. Dashboards 810 and 820 are alternate dashboards for displaying data relevant to a patient with hyperglycemia. Dashboards 830 and 840 are alternate dashboards for displaying data relevant to a patient with hypoxemia.

Each dashboard 810, 820, 830 and 840 includes multiple window panes, such as the window panes 822, 832, 842, 844, 846, and 848. The various window panes of the dashboards contain information about the selected patient. For instance, the window pane 822 shows a list of drugs administered to the patient (e.g. drugs, dosages, and times), the window pane 832 shows the percentage of oxygen saturation in blood (SpO2) in a table of measurements, the window pane 844 shows an image of a patient's most recent chest x-ray, the window pane 846 shows a graph of the patient's respiratory rate over time, and the window pane 848 shows a graph of the patient's SpO2 level over time.

In some embodiments, each dashboard includes a patient list window (described further below), such as the patient list window 842 of dashboard 840. The patient list window 842 provides a list of the patients, recorded clinical data regarding each patient, computed scores generated from patient clinical data, and trends associated with the recorded data values and generated scores. In some embodiments, the patient list 842 is editable, selectable, or clickable. In other embodiments, the list of patient names is not considered part of the dashboard.

Figure 9A:
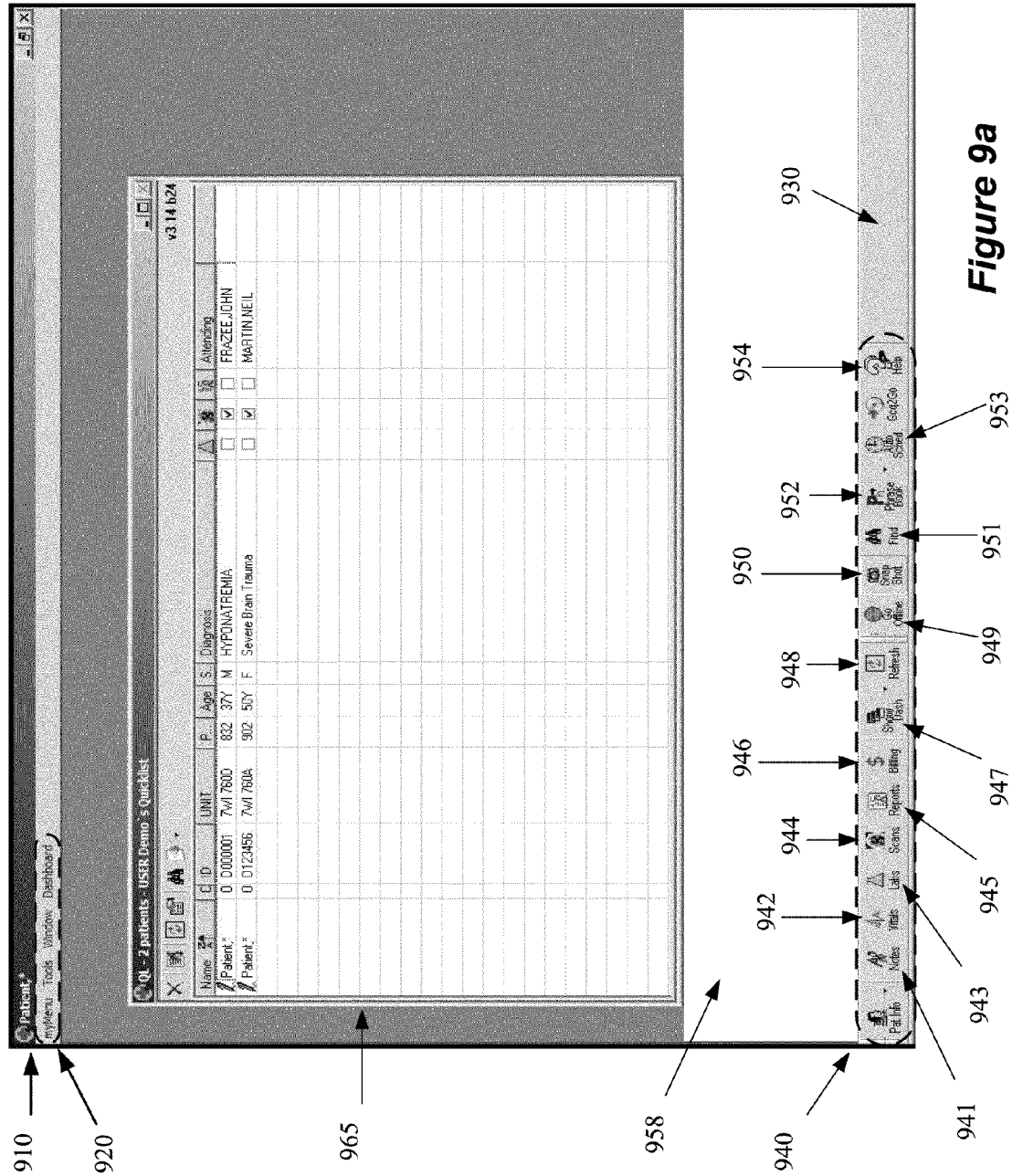
FIGS. 9a-9b illustrate a clinical information system (CIS) application user interface of some embodiments.
Figure 9B:
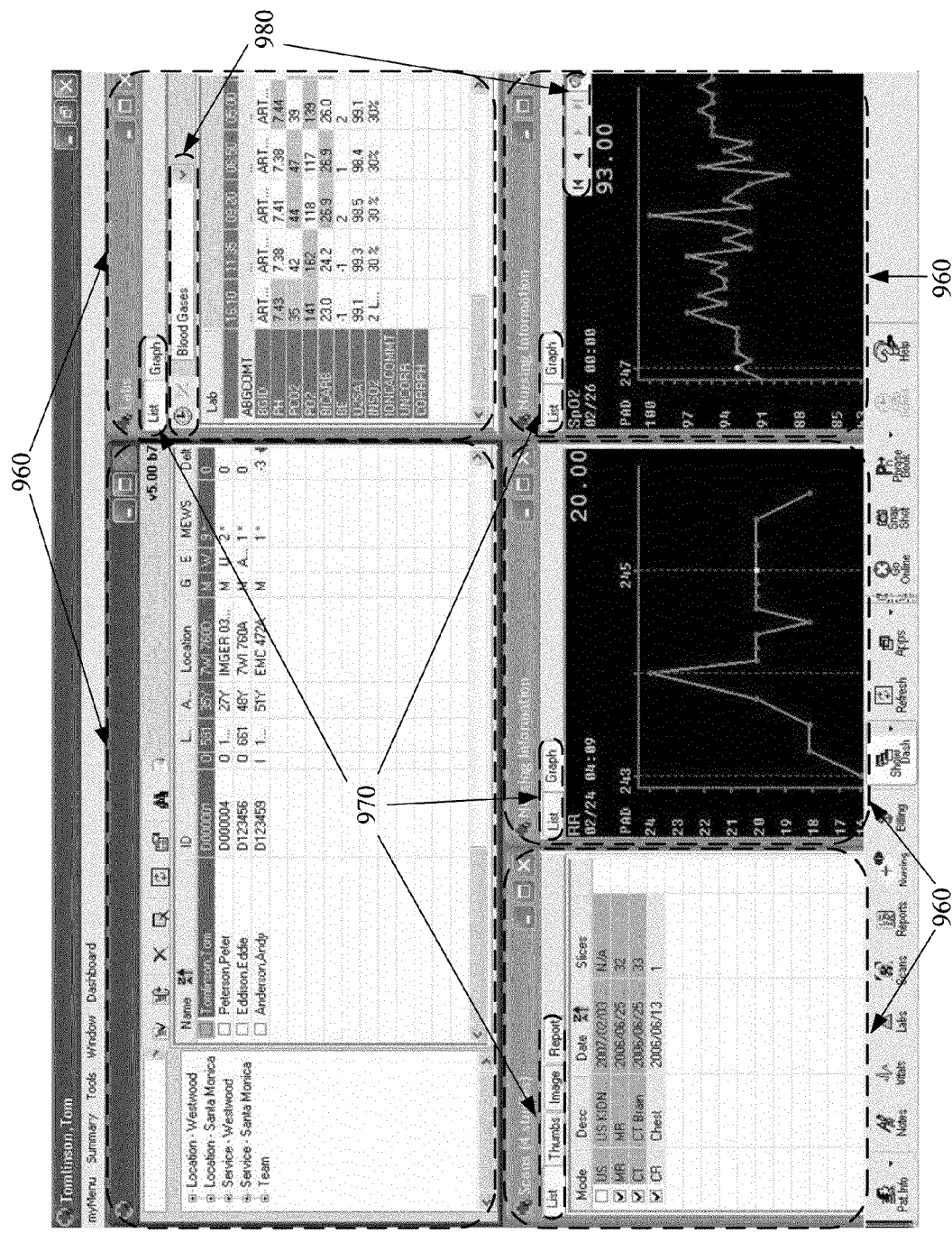

FIGS. 9a-9b illustrate a more detailed example of the user interface for a clinical information system (CIS) application user interface of some embodiments. In FIG. 9a, the user interface provides a master window 910 including a master window menu bar 920, master window toolbar 930, master window toolbar icons 940, master window viewing area 958, patient list 965, set of selectable tabs 970, and additional window pane toolbars and controls 980.

The master window 910 encloses the master window menu bar 920, master window toolbar 930, and master window viewing area 958. The master window menu bar 920 is located at the top of the CIS application user interface. The master window menu bar 920 lists available menu options for the CIS dashboard. When a menu bar option is selected (via a mouse click or appropriate keyboard sequence), the menu "pulls down," revealing a list of menu items or options. These options enable the user to perform various actions within the CIS dashboard. When working offline, some menu options are not available and are grayed out.

The master window toolbar 930 includes the master window toolbar icons 940. The master window toolbar 930 appears at the bottom of the CIS application and contains program icons 940 to access CIS dashboard functionality. When one of the master window toolbar icons 940 is selected, the corresponding function appears in the master window viewing area 958.

Available master window toolbar icons 940 in the master window toolbar 930 include a notes icon 941, a vital signs icon 942, a clinical labs icon 943, a scans icon 944, a reports icon 945, a billing icon 946, a show dashboard icon 947, a refresh icon 948, an applications icon (not shown), a go offline icon 949, a snap shot icon 950, a find icon 951, a phrase book icon 952, an auto schedule icon 953, and a help icon 954.

The notes icon 941 allows the user to enter clinical information into data entry forms or notes. The user can select from an existing list of notes designed by health care professionals. Examples of notes in the CIS Dashboard include the nursing notes and neurosurgery encounter note. The default for this button is called the default note and is configured via a menu item 955.

The vital signs 942 icon displays the patients near real-time vital sign data as monitored and communicated by the patient monitor. Data displays include but are not limited to (a) vital sign waveform data (i.e. multi-lead ECG, invasive blood pressure ART, PAP, CVP, etc., respiration, EtCO2, SpO2, CO), (b) trend data (i.e. line trends, tabular trend data), and (c) current vital parameters updated every few seconds.

The clinical labs icon 943 displays the patient's clinical lab data results as provided by the hospitals lab information system. Data views include but are not limited to (a) present day lab results, and (b) retrospective day-by-day lab results. Lab results are color coded into groups. Abnormally high values are highlighted in purple, low values are highlighted in blue, and normal values are not highlighted. Lab results can be viewed in tabular format and line trends.

The scans icon 944 displays the patient's radiology images as provided by the PACS. Radiology data types include but are not limited to (a) X-ray images, (b) MRI scans, (c) CT scans, (d) PET scans, (e) Dynamic Images (Cine Mode) and (f) Echo Cardiac Ultrasound. The CIS medical image application program provides a standard PAC image viewer the ability to manipulate images (i.e. zoom, rotate, pan, contrast, inversion).

The reports icon 945 displays a list of patient specific reports. These include but are not limited to scanned text records, orders, and reports in portable document format ("PDF"). The billing icon 946 displays the user-defined form (e.g., a neurosurgery encounter form). The default for this button is called the charge capture form and is configured via the menu item 955. The show dashboard icon 947 displays the default configuration of dashboard windows in the viewing area. The pull-down arrow displays a listing of available dashboard configurations for selection.

The refresh icon 948 allows the user to manually reload or update the patient data presented in the CIS dashboard. The applications icon (not shown) allows the user to open an external application (e.g., a drug reference database) to the CIS dashboard. The external application runs in a separate window on the user's computer. The go offline icon 949 allows the user to toggle the state of the application from online state to offline state and back without logging in and logging off. The snap shot icon 950 allows the user to capture and save the information on the screen. The user can select to capture the full screen or only the active window.

The find icon 951 allows the user to search and locate one or more patient based on user-specific criteria. The selected patients can then be added to a quick reference list. The phrase book 952 icon allows the user to enter commonly used phrases when entering patient data into notes. The phrases are created and saved by the user and available in all text forms involving editing.

The auto schedule 953 icon allows the user to set automatic patient data downloads to the computer or handheld device activated at a user-defined schedule. The help icon 954 displays online help, which provides assistance in the use of the application.

Toolbar buttons 940 are different in different embodiments. Depending upon the configuration of a CIS, some of the application buttons may not be loaded on the interface. In some embodiments, some menu options are not available and are grayed out a user is using the interface offline.

The master window viewing area 958 is the main area of the CIS dashboard that displays a patient list 965 containing patient information from various other hospital systems. In some embodiments, the master window viewing area 958 includes smaller windows called window panes. For instance, in FIG. 9b, there are multiple window panes 960 displayed in the viewing area 958. Each of the window panes 960 can be arranged, resized, or managed by the user. In some embodiments, a user can click within the pane to modify data, sort data, copy, paste, or drag and drop data. The set of window panes 960 collectively comprise a CIS dashboard of the illustrated embodiment.

The window panes 960 are displayed in the master window viewing area of the CIS dashboard and present patient information collected and integrated from a variety of clinical systems. Each of the window panes 960 includes a set of selectable tabs 970, additional window pane toolbars, and controls 980.

The clinical data content of a window pane can be called a window pane "view." Some window panes are capable of displaying more than one different view. In some embodiments, selectable tabs 970 affect what view a window pane displays. For example, the set of selectable tabs 970 at the top of a window pane allow a user to select different views presenting different clinical data. For a single view, there can be additional window pane toolbars and controls 980 to sort and navigate the clinical data presented. In some embodiments, such a CIS system includes an intelligent dashboard system for providing suggestions of dashboards to a user.

B. Patient List

As shown in FIG. 1, the CIS dashboard of some embodiments includes a patient list 100, as shown in FIG. 1, where the patient list 100 is displayed in its own separate window pane. The patient list 100 has several rows and columns. In some embodiments, each row displays an entry for a single patient. Rows 105, 130, 135, and 155 are examples of rows for exemplary patients John Doe, Jane Doe, Jim Doe, and Jean Doe. Each column displays a value containing certain information about the patient. Patient column 110 shows the name of each patient. Administrative column 115 displays administrative data, which can include information such as location, patient ID number, or other information. Severity score column group 120 and recorded data column group 125 display patient information. These column groups each display patient data, as well as trends associated with the data. A column for which there is no data available is blank or displays a placeholder value.

Column group 120 displays information about severity scores. The group 120 displays several types of severity scores: MEWS, SAPS II, and APACHE II. The score itself 140 and a trend (or "Δ") 145 are displayed. An arrow 150 indicates direction of change for the trend. An "up" arrow indicates an increase, while a "down" arrow indicates a decrease. For example, the list 100 displays that John Doe currently has a MEWS score of 11, but the score was previously 12. The columns of column group 125 display other patient recorded data, namely heart rate, blood pressure, glucose level, temperature, respiratory rate, AVPU score, oxygen saturation, and urine output. A trend for each recorded data value is also displayed in the list next to each recorded data value described by the trend. In some embodiments, the information displayed in the list 100 is updated regularly in order to provide a snapshot of each patient's health. In some embodiments, the updating of the list is done in an automated fashion.

In some embodiments, the list is sortable by any of the columns in order to allow efficient prioritization of health care and to facilitate discharging of patients. For example, FIG. 2 shows a list 200, which is the list 100 from FIG. 1 sorted by MEWS severity score. FIG. 3 shows a list 300 that is sorted by trend of MEWS severity score. In some embodiments, the heading of the sorting column 205 and 305 is highlighted to indicate that the list is sorted by that column.

Figure 10:
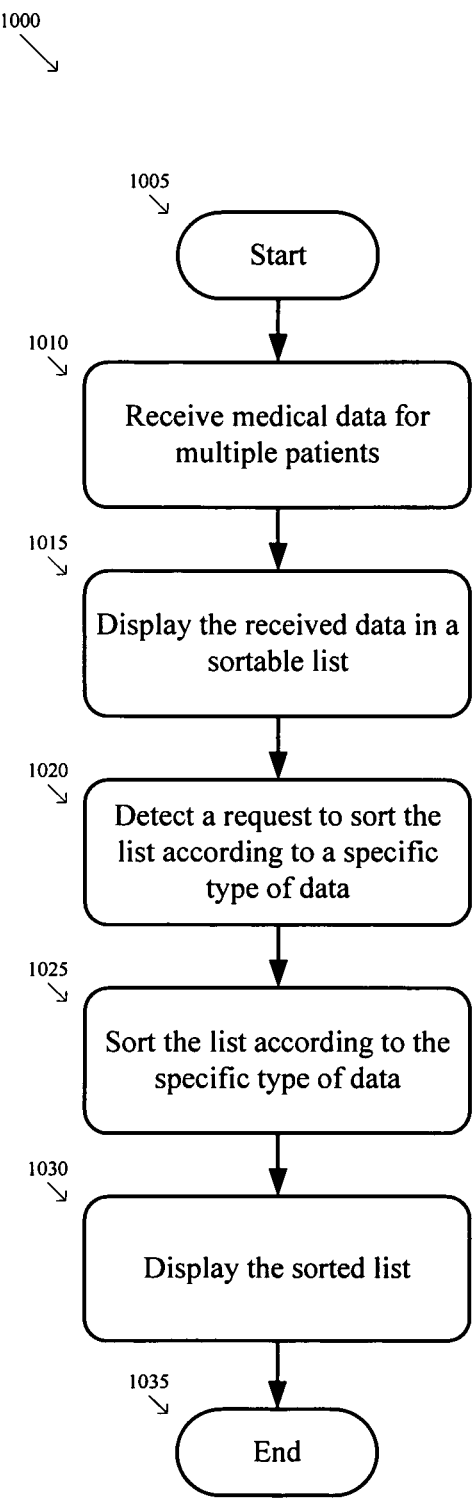
FIG. 10 illustrates a method that receives and displays data pertaining to multiple patients in a sortable list in accordance with some embodiments of the invention.

FIG. 10 illustrates a process 1000 in accordance with some embodiments that receives and displays medical data in a sortable list. After the process starts (at 1005), the process receives (at 1010) medical data for multiple patients. In some embodiments, the medical data includes aggregated and calculated patient data including a combination of severity scores, recorded data values, and trends, as discussed above. The process 1000 displays (at 1015) the received data in a sortable patient list in accordance with some embodiments. The process 1000 detects (at 1020) a request to sort the list according to a specific type of data. The process 1000 sorts (at 1025) the list according to the specific type of data and displays (at 1030) the resulting sorted list. The process 1000 ends at 1035.

Figure 11:
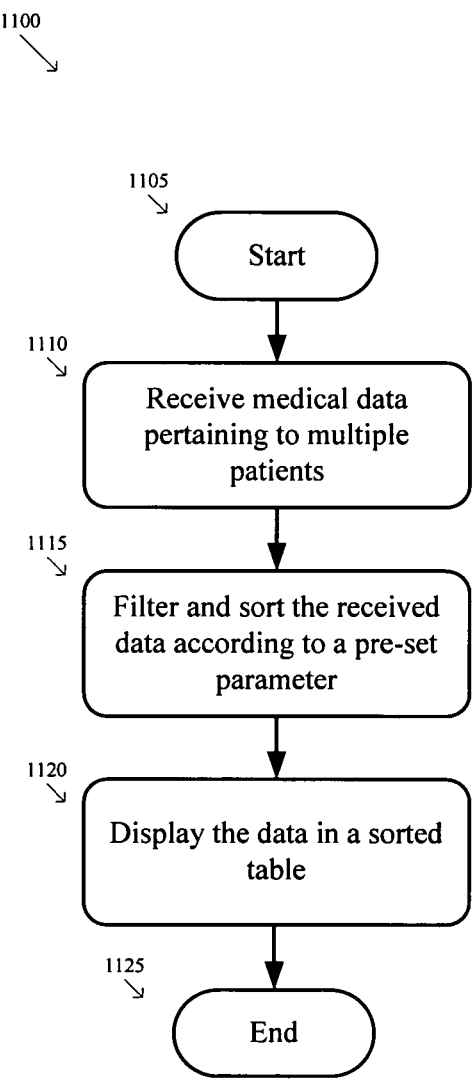
FIG. 11 illustrates an embodiment of a method that receives patient data and displays a pre-sorted list.

In some embodiments, the list is filtered and pre-sorted according to pre-set parameters before being displayed. FIG. 11 illustrates a process 1100 by which such a list is displayed in accordance with some embodiments. After the process 1100 starts at 1105, the process receives (at 1110) medical data pertaining to multiple patients. In some embodiments, the medical data is a combination of severity scores, recorded data values, and trends.

At 1115, the process 1100 filters and sorts the received data according to a pre-set parameter. In some embodiments, this parameter is a category of the received data. In some embodiments, the parameter is defined by a healthcare professional who views the list. One example of filtering and sorting is as follows. The CIS of some embodiments displays a complete set of patient data (including recorded vitals, scores, and their associated trends) to multiple teams in a hospital. One of these teams might be a team that monitors heart attack patients. This team might have specified a set of parameters in its CIS client application that requires the data that it views to be filtered for heart attack patients and sorted based on a particular vital sign, score, or trend of the vital sign or score.

After sorting and filtering the data, the process 1100 then displays (at 1120) the data in a patient list that is sorted in accordance with the pre-set parameter. In the above example of the team monitoring heart attack patients, the process would display a filtered and sorted list of all heart attack patients sorted by a particular vital sign, score, or trend. The process 1100 then ends at 1125. Even though the process 1100 performs both filtering and sorting operations, one of ordinary skill in the art should realize that in other embodiments, this process might only perform a sort operation or a filter operation.

FIGS. 1, 2, and 3 are set forth as illustrative examples of a patient list, but other embodiments have different combinations of the details discussed above. For example, some embodiments list only one type of severity score. Other embodiments do not contain a severity score column group 120. Some embodiments do not display a recorded data column group 125. Still other embodiments exhibit a less than one-to-one ratio between values and their associated trends (i.e.: some embodiments do not show trends for all values, while some embodiments do not show values for all trends). Some embodiments do not use arrows to indicate direction of change for trends. Some embodiments use positive and negative signs to indicate direction of change for trends. Some embodiments only show trends. Some embodiments do not show trends. Some embodiments display other types of severity scores. In some embodiments, the list can only be sorted by certain of the displayed columns. In some embodiments, the list is fully customizable to display only information that is relevant to a particular healthcare professional viewing the list. In some embodiments, the list is displayed on an interface 430. In other embodiments, the list is displayed on more than one interface 430.

C. Uses of a Patient List

1. Sorted Patient List

Sorted patient lists can be used by healthcare professionals to efficiently prioritize care of patients. For example, a doctor making rounds in a hospital may use a sorted patient list to determine the order in which she visits patients. A patient being displayed higher on the list may indicate that the patient needs more urgent attention than a patient who is displayed lower on the list, and thus should be visited first.

Another example of a use of a sorted patient list is by a hyperglycemia team. The hyperglycemia team is responsible for monitoring glucose levels in patients. A high glucose level may indicate a condition that requires swift action by the hyperglycemia team. FIG. 12 illustrates a sorted patient list 1200 of some embodiments that the hyperglycemia team may use. In this example, the list 1200 is sorted by glucose level 1205. FIG. 13 illustrates another sorted patient list 1300 of some embodiments that the hyperglycemia team may use. In this example, the list 1300 is sorted by glucose level trend 1305. Using one or both of these lists 1200 and 1300, the hyperglycemia team can predict or quickly respond to a glucose-related emergency requiring their attention.

Another example of a use of a sorted patient list is by an infectious disease team responsible for monitoring and preventing outbreaks of infectious diseases. FIG. 14 illustrates a sorted patient list 1400 of some embodiments that the infectious team may use. In this example, the list 1400 is sorted by temperature 1405. FIG. 15 illustrates another sorted patient list 1500 of some embodiments that the infectious disease team may use. In this example, the list 1500 is sorted by temperature trend 1505. Using one or both of these lists 1400 and 1500, the infectious disease team can predict or quickly respond to an infectious disease-related emergency requiring their attention.

Yet another example of a use of a sorted patient list is by a team responsible for determining when a patient should be discharged from a particular unit of a hospital. The team can determine whether a patient in a unit that provides a certain level of care should be discharged to a unit that provides a lower level of care. For example, the team may decide to discharge a patient from an ICU to an intermediary step-down unit or a general ward if the patient's condition is stable and/or improving. The team may also decide to discharge or recommend the discharge of a patient from a hospital altogether. Such a team may choose to sort the list by temperature, as patients with abnormal temperatures generally should not be discharged. The team may also choose to sort a list by severity score to view the overall condition of multiple patients.

An example of such a team is a discharge planning team that is associated with one unit or a fewer number of units than a bed control team. Another example of a team responsible for discharging patients is a bed control team. A bed control team is also responsible for managing availability of beds within a hospital and placing patients in available beds. Using a sorted patient list, such a bed control team can quickly see where beds are available for placing patients who need the beds.

Still another example of a use for a sorted patient list is in allocating resources to different units of a hospital or hospitals. In some cases, these resources include nurses, interns, physicians, technicians, intensivists, or other healthcare professionals. For instance, if the patient list shows that a unit has a high number of critical patients on a particular day, then the hospital administrators can assign a larger number of nurses to that unit.

The administrative column 115 in some embodiments includes location information for patients. For instance, the list can be sorted by patient location in order to view how many critical patients are in particular units of a hospital. A unit with a lower number of critical patients would be provided fewer resources than a unit with a higher number of critical patients. In some embodiments, the same concept is applied for allocating resources to several hospitals (i.e., providing fewer resources to a hospital with a lower number of critical patients than a hospital with a higher number of critical patients).

2. Customized Patient List

In some embodiments, the patient list can be customized. A customized patient list can be used by teams of healthcare professionals who are responsible for monitoring specific health parameters of patients. The hyperglycemia team may customize the list to only display severity scores, glucose levels, and trends associated with each. FIG. 16 illustrates such a list 1600. While a normal patient list of some embodiments displays MEW, SAPS, APACHE, glucose level, heart rate, blood pressure, urine output, and other patient health statistics, the list 1600 displays only information that a hyperglycemia team would find most important. Namely, the list 1600 displays MEWS, MEWS trend, SAPS, SAPS trend, APACHE, APACHE trend, glucose level, and glucose level trend.

Another example of a customized list is for an infectious disease team, who may choose to monitor only temperature and the trend of the temperature. Customized sorted patient lists can also be used when discharging patients from a unit of a hospital. A bed control team responsible for determining whether a patient should be discharged from a unit may choose to view severity scores and temperatures only.

In some embodiments, a data recipient 430, 435, or 440 displays only a portion of patient data supplied by a dissemination engine 425. In other embodiments, a dissemination engine 420 only disseminates a portion of recorded or calculated data. In some embodiments, customization is based on a set of pre-defined parameters. These pre-defined parameters are set by a user who views the customized patient list in some embodiments.

3. Automatic Generation of Sorted List

Figure 17:
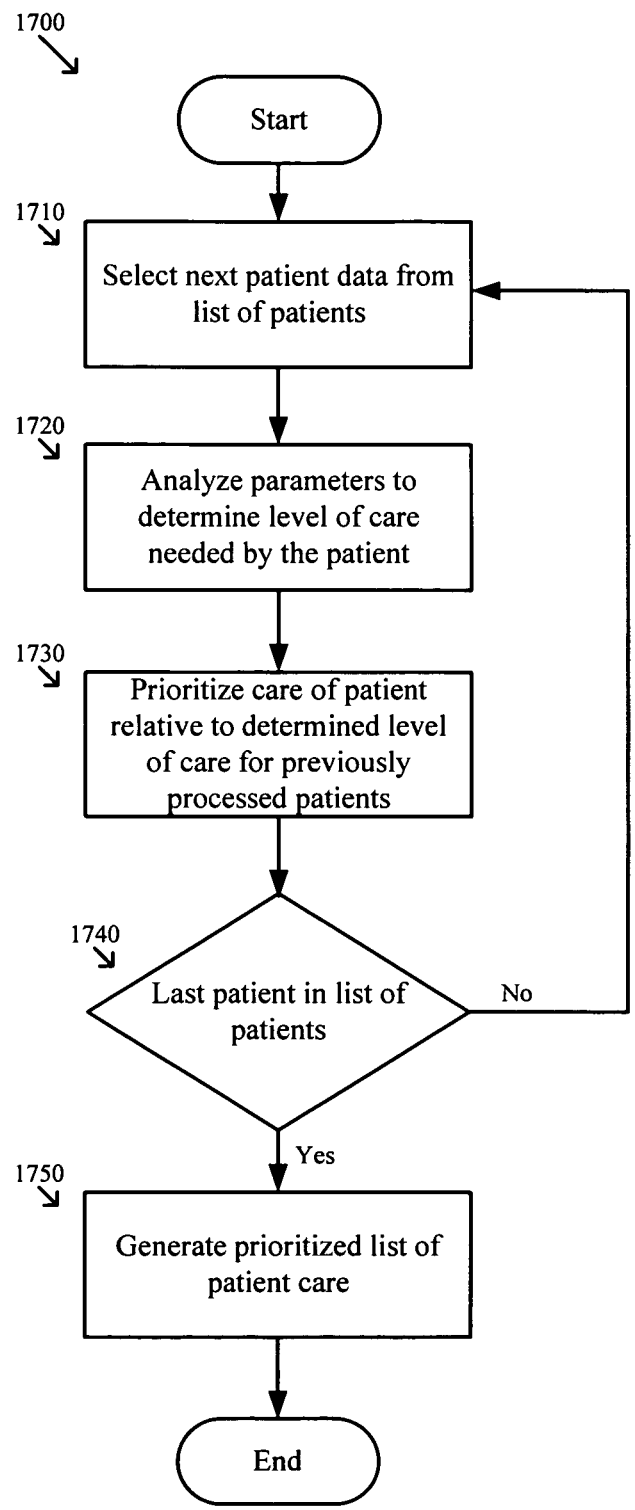
FIG. 17 illustrates an embodiment of a method for intelligently generating a prioritized list of patients.

In some embodiments, the patient lists include a pre-prioritized list of patients and their conditions. FIG. 17 presents a process 1700 for generating the prioritized list of patients based on their conditions. The process 1700 begins by selecting (at 1710) patient data for a patient within a list of patients. The process analyzes (at 1720) parameters within the selected patient data in order to determine the level of care needed by the patient. Some embodiments assign different weights to different parameters of the patient data and compute a unified score that quantifies the condition of the patient. The process then prioritizes (1730) the level of care needed by the selected patient. Some embodiments perform the prioritization by comparing the patient's required level of care to a set of previously analyzed patient data for a previous set of patients of the list that were analyzed.

The process then determines (at 1740) whether additional patients within the patient list remain to be analyzed. If additional patients remain, the process selects (at 1710) the data associated with the next patient in the list and the process again performs steps 1720-1740 on the selected patient data. If no additional patients remain, the process generates (at 1750) a prioritized list for treating the patients with those patients requiring the most urgent care appearing first within the prioritized list. The automatically generated prioritized list can be customized in accordance with some embodiments described above.

D. Drill-Down of Patient Data

Some embodiments allow a user to "drill down" to view more information about a recorded value (e.g., vital sign), calculated score, or trend. In order to display this detailed information, a dashboard comprising a window pane or a collection of window panes is displayed. There are many ways to present detailed information. Two such examples are a component view and a graph view, both of which are discussed below. Briefly summarized, a component view allows a user to select a calculated score (e.g. a severity score) for a patient and view the sub-components of the score. A graph view allows a user to view any quantitative value (e.g., a recorded value, calculated score, or trend) pertaining to the patient over a period of time.

1. Component View

Some embodiments provide a more detailed view of severity scores. FIG. 18 shows one embodiment of a component view 1800 of a severity score. Specifically, view 1800 shows a component view 1800 of patient Jane Doe's MEWS score. This particular embodiment displays patient name 130, MEWS score 1805 and MEWS trend 1810. A component view 1800 is useful because it provides a healthcare provider with specific information regarding driving factors behind a value or trend of a severity score. For example, Jane Doe's MEWS score displays a value 1805 of 5 and a trend 1810 of an increase of 2. While this information can provide insight to her condition, the sub-scores of elements of the severity score, and sub-trends 1815 provide even more detailed insight. The sub-scores show that her AVPU score has increased from 0 to 3, and that her respiratory rate sub-score has decreased from 3 to 2, thus providing a net increase in MEWS score from 3 to 5. The drill-down view 1800 in some embodiments can display severity score, severity sub-scores, and trends of other severity scores, such as APACHE II or SAPS II.

As described at length in concurrently filed U.S. patent application "Multi-Automated Severity Scoring," and shown in FIG. 19, MEWS is calculated from five elements: blood pressure, heart rate, respiratory rate, temperature, and AVPU score. MEWS scores range from zero (least severe) to fourteen (most severe). The component view 1800 displays a value for each individual element from which the MEWS severity score is calculated. The component view 1800 also displays trends for each displayed element.

The view 1800 further shows a sub-score and trend 1815 for each individual element to show how the element directly contributes to the severity score. The displaying of individual sub-scores and their trends allows healthcare professionals to make more individualized and insightful diagnoses and to provide more appropriate treatment. Some embodiments also display a message 1820 indicating how the severity score is derived from the sub-scores. The message 1820 is useful in the case of a severity score that is not merely the sum of its sub-scores.

In some embodiments, a component view 1800 is shown in a separate window pane from a patient list 100. In some embodiments, the separate window is displayed upon a mouse or keyboard command from a user. In some embodiments, the component view 1800 is displayed when a severity score is right-clicked. In some embodiments, the component view is fully customizable to remove any of the features discussed above, or to add additional features.

2. Graphs

Figure 20:
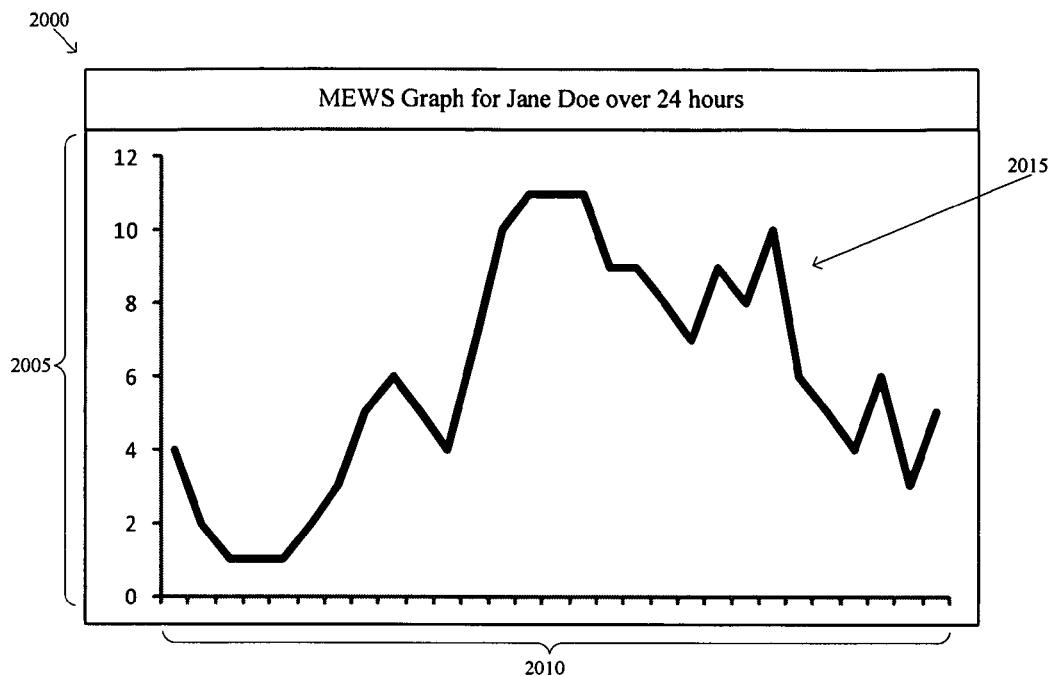
FIG. 20 illustrates a graph showing severity score versus time.

FIG. 20 illustrates another example of a detailed view 2000 that can be used in some embodiments to provide insight as to a patient's condition. The detailed view provided in this example is a graph 2015 that displays MEWS scores for Jane Doe over a period of time (e.g., a few minutes or hours, one day, several days, etc.). The MEWS score is displayed on the Y-axis 2005, while the X-axis 2010 represents time. The graph 2000 can be used to show values of other severity scores (e.g., APACHE II or SAPS II) over time. In some embodiments, the graph 2000 shows recorded data values (e.g., heart rate, blood pressure, etc.) over time. In other embodiments, the graph 2000 displays components of calculated scores (e.g., an element of a MEWS score) over time. In some embodiments, the period of time displayed is customizable by a healthcare provider.

Figure 21:
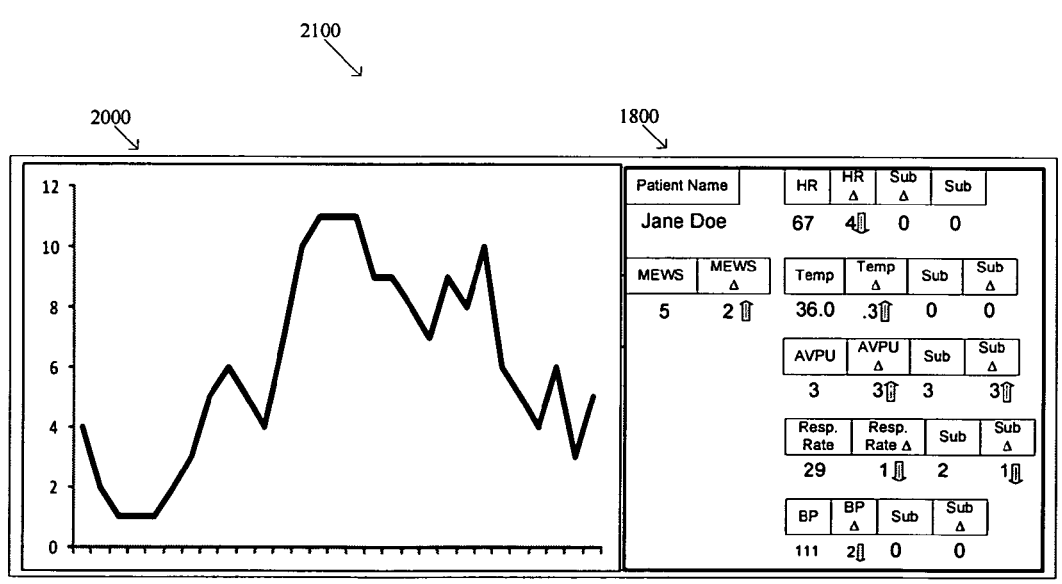
FIG. 21 illustrates a view that shows the graph of FIG. 20 and the drill-down view of FIG. 18 in the same window pane in accordance with some embodiments.

In some embodiments, a graph is shown in a separate window pane from a patient list or a component view. In other embodiments, a single command causes a graph to be displayed simultaneously with a component view. FIG. 21 illustrates some embodiments in which a graph 2000 and component view 1800 are displayed in the same window pane 2100. In other embodiments, the component view 1800 can be displayed simultaneously with the graph 2000, but in separate window panes. In these embodiments, the graph 2000 and component view 1800 are two window panes that together represent a dashboard that opens (e.g., opens upon the selection of the MEWS score). Some embodiments display multiple graphs and/or component views in one window pane or separate window panes.

Concurrently filed U.S. application Ser. No. 12/036,281, entitled "Drill-Down Dashboard,", which is hereby incorporated into this application by reference, also discusses methods and systems for displaying drill-down views. However, some of the drill-down views discussed above are distinct from those mentioned in "Drill-Down Dashboard." The views discussed above focus on displaying information granting insight into specifically requested health data value (e.g., a recorded value, score, or trend) for a patient, while the views discussed in "Drill-Down Dashboard" application are more tailored to the patient's overall condition. Some of these other dashboards are presented, for example, when a patient's name is selected.

E. Intelligent Diagnosis Prompt

Figure 22:
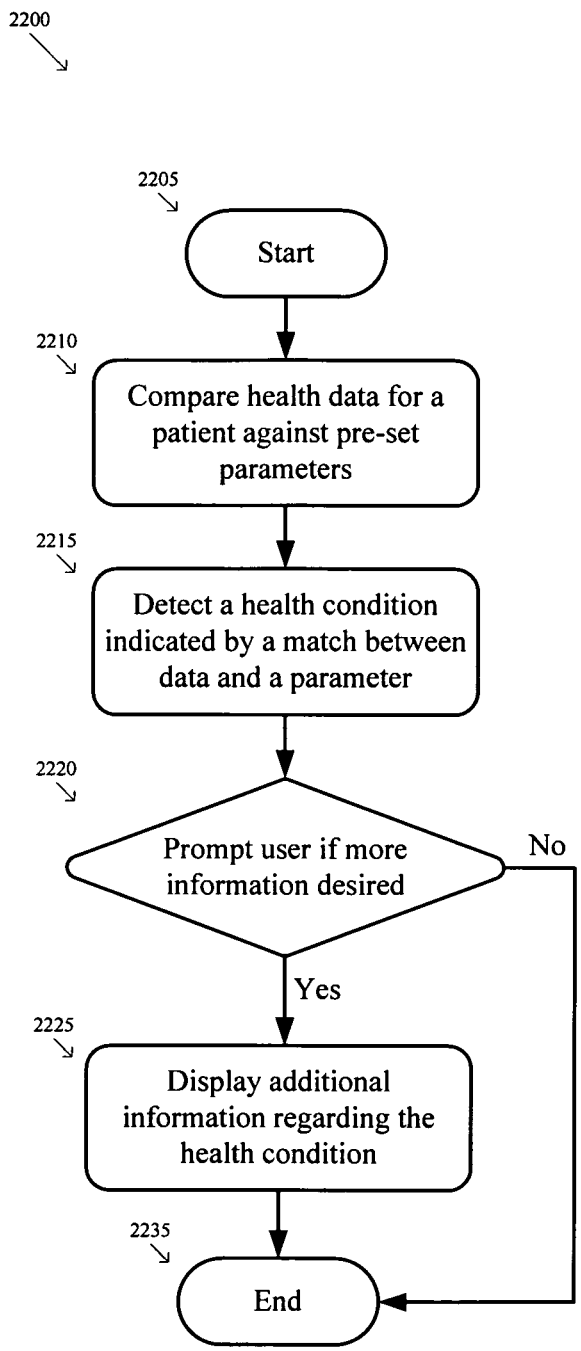
FIG. 22 illustrates an embodiment of a method for detecting a medical condition and displaying information about the medical condition.

In some embodiments, a process automatically detects predefined health conditions and provides an intelligent dashboard display providing more information about the health condition when desired. FIG. 22 describes such a process. The process 2200 starts (at 225), and compares (at 2210) a patient's health data against pre-set parameters. If the health data matches the parameters above a certain threshold, the process detects (at 2215) that a health condition may exist based on the match. The process then prompts (at 2220) a user to see if the user wants to view more information regarding. FIG. 23 shows an example of such a prompt 2300. If the user chooses to display more information, the process displays (at 2225) the additional data.

In some embodiments, the additional data includes more detailed patient history, medical charts, and treatment information for the specific condition. In some embodiments, the treatment information is further tailored to the specific patient (e.g., treatments that the patient is allergic to are not recommended). The process then ends (at 2235). More functionalities of an intelligent dashboard are described in concurrently filed U.S. patent application Ser. No. 12/036,287, entitled "Intelligent Dashboard."

IV. Automated Alerts

Some embodiments alert different medical care responders, such as rapid response teams, in an automated fashion based on the values or trends in one or more of the parameters representing a patient's health. Included within the alerts of some embodiments is pertinent data that causes the alert and that is needed by a responder in order to diagnose a condition and provide the proper treatment to restore the patient's health. Such automated alerts assemble responders quickly prior to or during the worsening of a patient's condition such that the patient receives more timely treatment that could reduce the severity of the condition or prevent the condition from occurring.

Some embodiments issue the alerts via e-mail, Short Message Service (SMS), paging system of the medical care provider, or other audible alarms within the medical care provider. Each manner of dissemination may include different protocols and wired or wireless means for issuing the alerts. Responders receive the alerts using hospital pagers, personal digital assistants (PDAs), pagers, smartphones, cellular telephones, or other electronic devices.

Some embodiments issue the automated alerts based on a value of a single parameter or a change that occurs within single parameter over a particular temporal interval. For example, some embodiments determine that when glucose levels for a patient recovering from a surgical procedure exceed specified thresholds, responders should be alerted to address the perceived change in the patient's condition. Some embodiments issue the automated alerts based on values of a set of parameters or changes in the values of the set of parameters where the set of parameters together may represent the value of a severity score.

Figure 24:
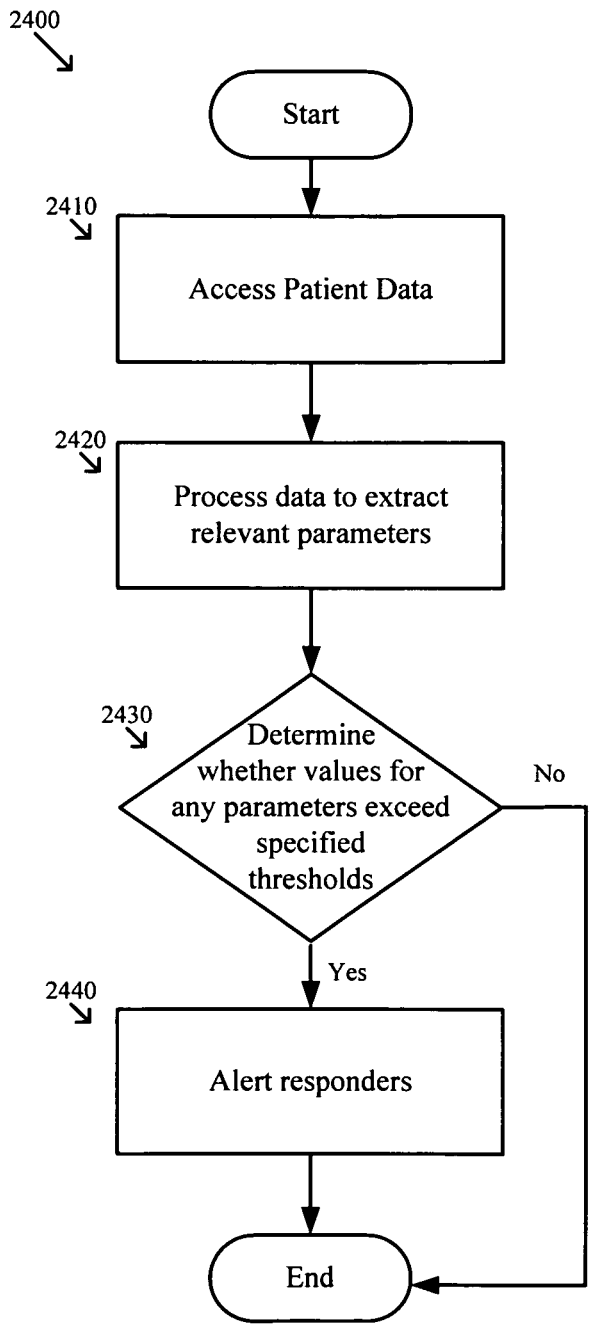
FIG. 24 illustrates an embodiment of a method for providing an alert when a medical event occurs.

FIG. 24 presents a process 2400 for issuing alerts based on data related to a patient's condition. The process 2400 begins by accessing (at 2410) patient data. In some embodiments, the patient data is stored within a centralized database and therefore the process 2400 must pull the data from the database. In other embodiments, the process 2400 is a process that runs locally within the database or is a process that is executed as the data is entered into the database in real-time. In still other embodiments, the process 2400 is a process that directly executes within a monitor linked to the patient in order to monitor one or more health conditions of the patient.

Once the data is accessed, some embodiments process (at 2420) the accessed data in order to analyze one or more particular parameters within the accessed data. The process then determines (at 2430) whether values for any of the one or more particular parameters exceed predefined thresholds for the parameters. In some embodiments, the process analyzes the trends of the parameters to determine whether a change in the values of parameter is significant enough to indicate a worsening of the patient condition. In either case, exceeding the threshold causes the process to issue (at 2440) an alert to one or more responders.

In some embodiments, the issued alert contains the parameters at issue so that the responder is notified of the issue prior to arriving at the scene of the condition. Moreover, some embodiments include related information in addition to the parameter at issue. These additional parameters may include parameters related to a condition for which the patient was admitted or is undergoing treatment for. For example, an alert for a patient experiencing heart related issues due to a sudden change in heart function will include the heart rate parameter causing the alert as well as other heart related parameters such as blood pressure, blood oxygen levels, etc. Accordingly, the additional parameters sent in conjunction with the alert are dynamically determined based on the condition at issue.

In some embodiments, the alert is issued to medical care professionals assigned to treat the patient, whereas some embodiments issue intelligent alerts that dynamically alert different responders based on the particular parameter exceeding the threshold. In this manner, some embodiments are able to target specialized responders based on the parameter. For example, if the parameter at issue is a heart-related parameter, then some embodiments issue the alert to a cardiologist. If the parameter at issue is a neurological related parameter then some embodiments issue the alert to a neurologist. If the patient is in an intensive care unit (ICU), then some embodiments alert an intensivist.

V. Computer System

In some embodiments, the collection engine 410, calculation engine 415, and dissemination engine 425 are software modules on a server. In some embodiments, the server includes one or more computers having volatile memory, non-volatile memory, at least one processor, a wired or wireless network card, and at least one input/output device. In some embodiments, the server runs an operating system such as Microsoft Windows, UNIX, LINUX, or Mac OS. In some embodiments, the server receives patient data through a wired local area network (LAN) connection or a wireless LAN (WLAN) connection. In some embodiments, the server receives patient data through a connection to the Internet. In some embodiments, the server supplies patient data to an interface through LAN, WLAN, or the Internet.

In some embodiments, the interface 430 is located on a device that has volatile memory, at least one processor, a wired or wireless network card, and an output device that is capable of displaying data visually. In some embodiments, the device has non-volatile memory. In some embodiments, the device is one of a laptop computer, a desktop computer, cellular phone, mobile device, smartphone, pager, personal digital assistant (PDA), or any other electronic device. In some embodiments, the device is connected to a printer that is capable of printing data displayed by the interface 430.

Figure 25:
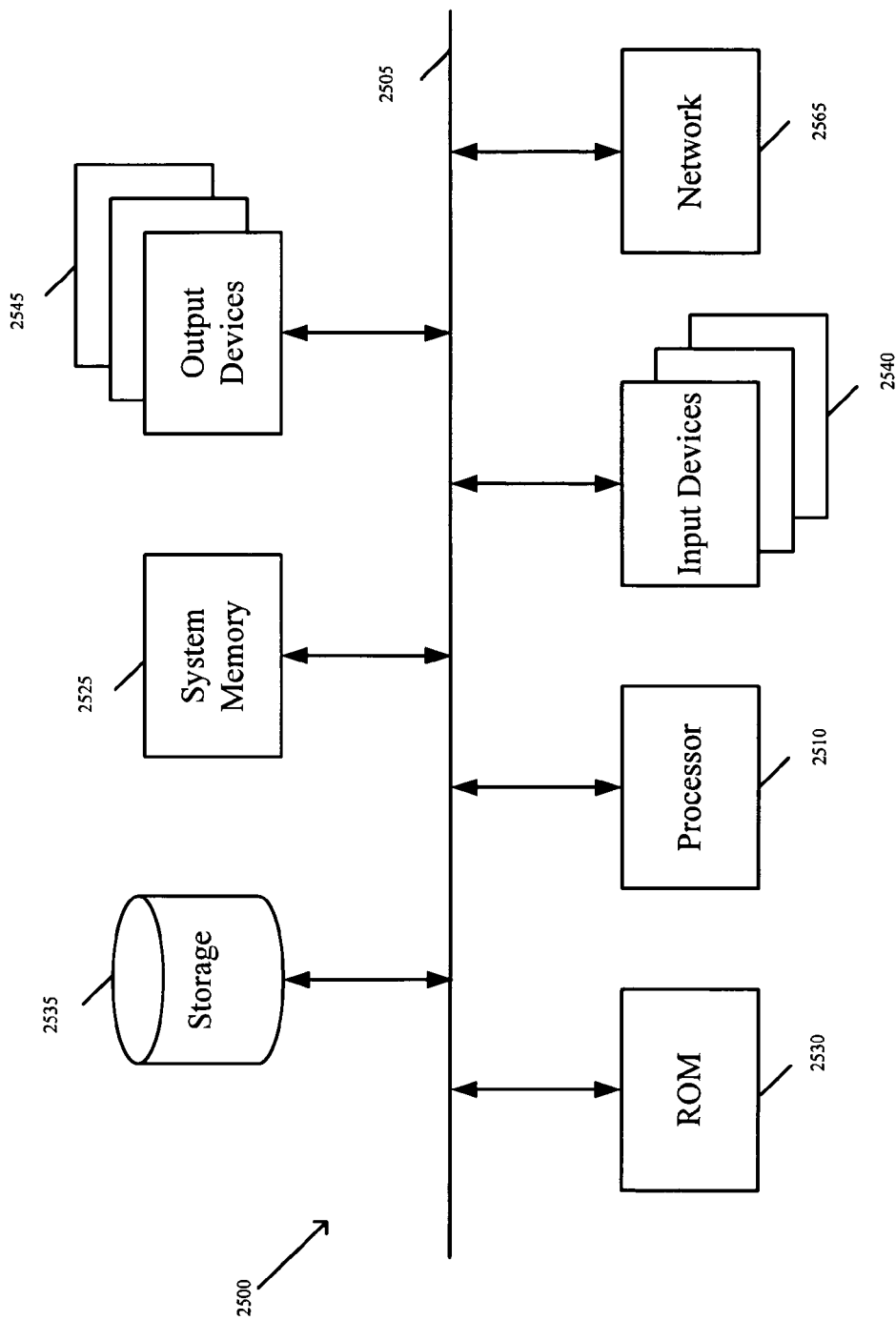
FIG. 25 conceptually illustrates a computer system of some embodiments.

FIG. 25 illustrates a computer system with which some embodiments of the invention are implemented. Computer system 2500 includes a bus 2505, a processor 2510, a system memory 2525, a read-only memory 2530, a permanent storage device 2535, input devices 2540, and output devices 2545.

The bus 2505 collectively represents all system, peripheral, and chipset buses that communicatively connect the numerous internal devices of the computer system 2500. For instance, the bus 2505 communicatively connects the processor 2510 with the read-only memory 2530, the system memory 2525, and the permanent storage device 2535.

The various memory units 2525, 2530, and 2535 are parts of the computer system's 2500 computer readable medium from which the processor 2510 retrieves instructions to execute and data to process in order to execute the processes of the invention. The read-only-memory (ROM) 2530 stores static data and instructions that are needed by the processor 2510 and other modules of the computer system. The permanent storage device 2535, on the other hand, is a read-and-write memory device. This device is a non-volatile memory unit that stores instructions and data even when the computer system 2500 is off. Some embodiments of the invention use a mass-storage device (such as a magnetic or optical disk and its corresponding disk drive) as the permanent storage device 2535.

Other embodiments use a removable storage device (such as a floppy disk or USB flash disk) as the permanent storage device. Like the permanent storage device 2535, the system memory 2525 is a read-and-write memory device. However, unlike storage device 2535, the system memory is a volatile read-and-write memory, such a random access memory. The system memory stores some of the instructions and data that the processor needs at runtime. In some embodiments, the invention's processes are stored in the system memory 2525, the permanent storage device 2535, and/or the read-only memory 2530.

The bus 2505 also connects to the input and output devices 2540 and 2545. The input devices enable the user to communicate information and select commands to the computer system. The input devices 2540 include alphanumeric keyboards and pointing devices. The output devices 2545 display images generated by the computer system. For instance, these devices display a graphical user interface. The output devices include printers and display devices, such as cathode ray tubes (CRT) or liquid crystal displays (LCD).

Finally, as shown in FIG. 25, bus 2505 also couples computer 2500 to a network 2565 through a network adapter (not shown). In this manner, the computer can be a part of a network of computers (such as LAN, WLAN, a wide area network ("WAN"), an intranet, or a network of networks, such as the Internet. For example, the computer 2500 may be coupled to a web server (network 2565) so that a web browser executing on the computer 2500 can interact with the web server as a user interacts with a graphical user interface that operates in the web browser.

Any or all components of computer system 2500 may be used in conjunction with the invention. For instance, each of the computer readable memories of the computer system 2500 may function as one or more of the storages for some embodiments of the invention. One of ordinary skill in the art would appreciate that any other system configuration may also be used in conjunction with the present invention.

One of ordinary skill in the art will realize that the above described methods and systems yield numerous advantages. For instance, the methods and systems enable healthcare providers to better monitor patients and to provide an overview of health conditions of multiple patients to enable healthcare professionals to efficiently prioritize the care of patients throughout an entire hospital. A further advantage is enabling such prioritization throughout a chain of hospitals. Additionally, real-time alerts regarding patient health episodes are provided. Using real-time monitoring of recorded data, severity scores, and trends, rapid response teams will be able to respond more quickly and effectively when a patient suffers an episode requiring their care. Bed control teams will be able to discharge patients from a unit whose presence in the particular unit is not necessary, or whose needs are preempted by the needs of a patient who requires more urgent attention. Healthcare professional will also be able to admit a patient to a more intensive unit sooner by virtue of easily identifying that the patient requires more immediate care than she is presently receiving.

One of ordinary skill in the art would realize that some of the features described in this application are present in prior art. However, they have not been used in combination with other features described herein. Furthermore, while the invention has been described with reference to numerous specific details, one of ordinary skill in the art will recognize that the invention can be embodied in other specific forms without departing from the spirit of the invention. Thus, one of ordinary skill in the art would understood that the invention is not to be limited by the foregoing illustrative details, but rather is to be defined by the appended claims.

The invention claimed is:

1. An automated method for monitoring a plurality of patients to prioritize patient care in a least two hospitals, the method comprising:
   receiving an unsorted listing of a plurality of clinical data for a plurality of patients from a server through a connection to the Internet, the server receiving the plurality of clinical data from the at least two hospitals;
   sorting the unsorted listing of the plurality of clinical data using software executing on the server;
   calculating severity scores from said plurality of clinical data using software executing on the server;
   providing a unified display for displaying said clinical data and said severity scores; and
   displaying said clinical data and said severity scores on a unified display,
   wherein said unified display is sorted based on a condition to monitor,
   wherein said unified display displays at least two numeric severity scores associated with the clinical data for each patient,
   wherein each said severity score is based on at least two components of clinical data, and
   wherein the server is located at one hospital and performs the steps of receiving an unsorted list, sorting the unsorted list, and calculating the severity scores for the at least two hospitals.

2. The method of claim 1, wherein the step of sorting the unsorted listing of the plurality of clinical data is based on a user request that specifies the condition to monitor through a particular sorting of the clinical data.

3. The method of claim 1, wherein the step of sorting the unsorted listing of the plurality of clinical data is according to a configuration setting that specifies a condition to monitor through a predetermined sorting of the clinical data.

4. The method of claim 3, wherein the configuration setting comprises a stored user request that previously specified the condition to monitor through a particular sorting of the clinical data.

5. The method of claim 1, further comprising calculating trends associated with the data to include within the unified display of the data.

6. The method of claim 1, wherein the severity score is one of Acute Physiology and Chronic Health Examination (APACHE), APACHE II, Simplified Acute Physiology Score (SAPS), SAPS II, and Modified Early Warning Score (MEWS).

7. The method of claim 1, further comprising prioritizing care for a first patient over care for a second patient when the first patient's associated severity score and trend indicates that the first patient needs more urgent care than the second patient.

8. The method of claim 1 further comprising disseminating said unified display to a device of at least one different data recipient.

9. The method of claim 1, wherein the plurality of clinical data comprises at least two vital statistics of blood pressure, heart rate, urine output, respiratory rate, temperature, oxygen saturation, glucose level, and AVPU (Alert, reacting to Voice, reacting to Pain, Unresponsive) score.

10. The method of claim 1 further comprising providing a user interface tool for sorting said data according to data values of a particular parameter of the clinical data.

11. The method of claim 1, wherein the patients are in a single unit of a single hospital.

12. The method of claim 1, wherein at least two different patients are in two different units of a single hospital.

13. The method of claim 1, wherein at least two different patients are in two different hospitals.

14. An automated method for determining an order of patients to be discharged in one or more units of a hospital, the method comprising:
   providing a list of medical care receiving patients via software executing on a server;
   providing a set of clinical data and two or more numeric severity scores selected from the group of Acute Physiology and Chronic Health Examination (APACHE), APACHE II, Simplified Acute Physiology Score (SAPS), SAPS II, and Modified Early Warning Score (MEWS) for each patient via software executing on a server;

displaying the list of medical care receiving patients on a user interface;

sorting the list by at least one clinical data and one numeric severity score, the list being first unsorted and a configuration setting specifies a particular sorting of the list; and defining a set of patients to discharge from a unit of a hospital based on the particular sorting the data and scores, wherein the unit is at least one of an intensive care unit (ICU), an intermediary step-down unit, and a general ward of the hospital, and wherein each said severity score is based on at least two components of clinical data.

15. The method of claim 14 further comprising defining a set of patients that require immediate assistance from a rapid response team based on a particular sorting the data and scores.

16. The method of claim 15, wherein the defining the set of patients that require immediate assistance from the rapid response team comprises comparing values for the clinical data and the set of scores to a set of predefined threshold clinical data values and score values.

17. An automated method for monitoring patients in one or more units of a hospital, the method comprising:

aggregating a plurality of clinical data parameters for a plurality of patients using software executing on a server, wherein aggregating said plurality of clinical data parameters comprises calculating at least two numeric severity scores for each patient; and generating an automated alert for a particular patient when values for at least one of the severity scores for the particular patient exceed specified thresholds, the automated alert including said severity score;

identifying at least one responder based on a responder specialty and the particular severity score that exceeds the threshold; and transmitting the alert to the identified responder, wherein each said severity score is based on at least two components of clinical data, and wherein the alert is at least one of: an audible alarm, a pop-up message on a screen, a visual alarm, a pager message, an e-mail message, and a Short Message Service (SMS) message.

18. The method of claim 17, wherein said aggregated data parameters comprise at least two of a vital sign, a severity score, a first trend relating the vital sign to at least one earlier vital sign, and a second trend relating the severity score to at least one earlier severity score, wherein the specified thresholds specify acceptable value ranges for the vital sign, severity score, first trend, and second trend.

19. A graphical user interface (GUI) for presenting clinical data, said GUI comprising:

a display area for displaying a plurality of medical care receiving patients; and a list within the display area for providing at least one clinical data and at least two numeric severity scores associated with each patient, wherein the list is sortable by at least one of the clinical data and one of said severity scores, the list being first unsorted and a configuration setting specifies a particular sorting of the list, wherein the configuration setting comprises a stored user request that previously specified the condition to monitor through a particular sorting of the clinical data;

wherein the GUI is displayed on a user interface, the user interface comprising a tool for specifying a sorting of the patients and the list within the display area, and wherein each said severity score is based on at least two components of clinical data, wherein the clinical data and the at least two numeric severity scores are provided to the GUI via software executing on a server, the server receiving the clinical data from at least two hospitals.

20. The GUI of claim 19, wherein at least one of said severity scores is selected from a group of Acute Physiology and Chronic Health Examination (APACHE), APACHE II, Simplified Acute Physiology Score (SAPS), SAPS II, and Modified Early Warning Score (MEWS).

* * * * *